(12) United States Patent
Yen

(10) Patent No.: US 10,014,478 B2
(45) Date of Patent: Jul. 3, 2018

(54) INDENOTRIPHENYLENE-BASED DIAMINE DERIVATIVE AND ORGANIC ELECTROLUMINESCENCE DEVICE USING THE SAME

(71) Applicant: Feng-Wen Yen, Taipei (TW)

(72) Inventor: Feng-Wen Yen, Taipei (TW)

( * ) Notice: Subject to any disclaimer, the term of this patent is extended or adjusted under 35 U.S.C. 154(b) by 376 days.

(21) Appl. No.: 14/716,856

(22) Filed: May 19, 2015

(65) Prior Publication Data

US 2016/0343941 A1    Nov. 24, 2016

(51) Int. Cl.
| | |
|---|---|
| *H01L 51/00* | (2006.01) |
| *C07C 211/61* | (2006.01) |
| *C09K 11/06* | (2006.01) |
| *C07D 333/76* | (2006.01) |
| *C07D 307/91* | (2006.01) |
| *C07D 209/86* | (2006.01) |

(Continued)

(52) U.S. Cl.
CPC .......... *H01L 51/006* (2013.01); *C07C 211/61* (2013.01); *C07D 209/86* (2013.01); *C07D 307/91* (2013.01); *C07D 333/76* (2013.01); *C09K 11/025* (2013.01); *C09K 11/06* (2013.01); *H01L 51/0056* (2013.01); *H01L 51/0073* (2013.01); *H01L 51/0074* (2013.01); *C07C 2603/18* (2017.05); *C07C 2603/54* (2017.05); *C09K 2211/1007* (2013.01); *C09K 2211/1011* (2013.01); *C09K 2211/1014* (2013.01); *C09K 2211/1029* (2013.01); *C09K 2211/1088* (2013.01); *C09K 2211/1092* (2013.01); *H01L 51/5012* (2013.01); *H01L 51/5056* (2013.01); *H01L 51/5096* (2013.01)

(58) Field of Classification Search
CPC ........................................................ H01L 51/00
USPC ............................................................. 428/690
See application file for complete search history.

(56) References Cited

U.S. PATENT DOCUMENTS

| | | |
|---|---|---|
| 8,962,160 B2 | 2/2015 | Yen et al. |
| 8,993,130 B2 | 3/2015 | Yen et al. |
| 2013/0048975 A1 | 2/2013 | Hong et al. |

(Continued)

FOREIGN PATENT DOCUMENTS

| | | |
|---|---|---|
| WO | 2008062636 A1 | 5/2008 |
| WO | 2012091471 A2 | 7/2012 |

*Primary Examiner* — Duc Truong

(57) ABSTRACT

The present invention discloses an indenotriphenylene-based diamine derivative is represented by the following formula (1), the organic EL device employing the derivative as hole transport layer, electron blocking layer and fluorescent emitting dopant of emitting layer can display good performance like as lower driving voltage and power consumption, increasing efficiency and half-life time.

formula (1)

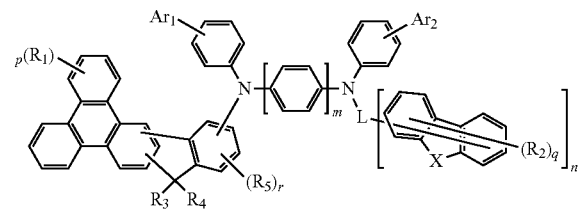

wherein $Ar_1$, $Ar_2$, L, X, m, n, p, q, r and $R_1$ to $R_5$ are the same definition as described in the present invention.

14 Claims, 1 Drawing Sheet

| | |
|---|---|
| 14 | — metal electrode |
| 13 | — electron injection layer |
| 12 | — electron transport layer |
| 11 | — hole blocking layer |
| 10 | — emitting layer |
| 9 | — electron blocking layer |
| 8 | — hole transport layer |
| 7 | — hole injection layer |
| 6 | — transparent electrode |

(51) Int. Cl.
*C09K 11/02* (2006.01)
*H01L 51/50* (2006.01)

(56) References Cited

U.S. PATENT DOCUMENTS

| | | |
|---|---|---|
| 2014/0151645 A1 | 6/2014 | Yen et al. |
| 2014/0175383 A1 | 6/2014 | Yen et al. |
| 2014/0209866 A1 | 7/2014 | Yen et al. |
| 2014/0231754 A1 | 8/2014 | Yen |

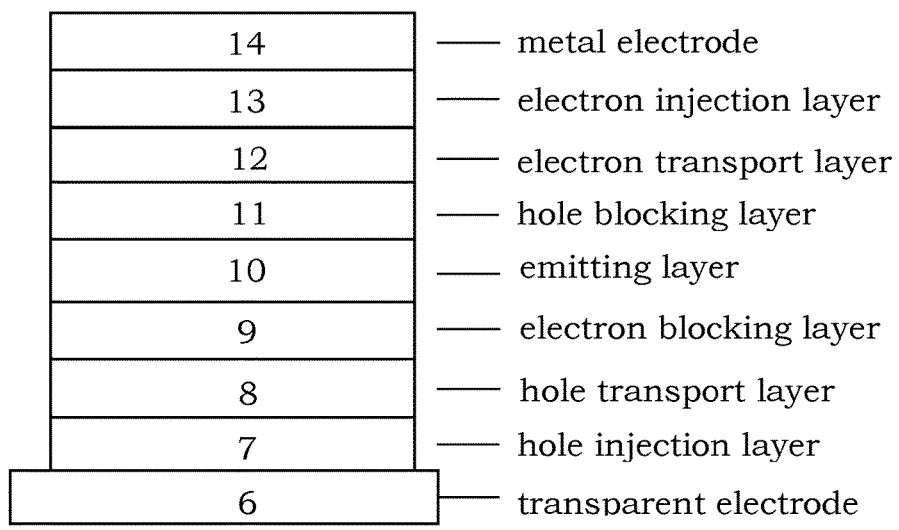

US 10,014,478 B2

INDENOTRIPHENYLENE-BASED DIAMINE DERIVATIVE AND ORGANIC ELECTROLUMINESCENCE DEVICE USING THE SAME

FIELD OF INVENTION

The present invention generally relates to an indenotriphenylene-based diamine derivative and organic electroluminescence (herein referred to as organic EL) device using the derivative. More specifically, the present invention relates to the indenotriphenylene-based diamine derivative having general formula (1), an organic EL device employing the derivative as hole transport layer, electron blocking layer and fluorescent emitting dopant of emitting layer.

BACKGROUND OF THE INVENTION

Organic electroluminescence (organic EL) is a light-emitting diode (LED) in which the emissive layer is a film made by organic compounds which emits light in response to an electric current. The emissive layer of organic compound is sandwiched between two electrodes. Organic EL is applied in flat panel displays due to their high illumination, low weight, ultra-thin profile, self-illumination without back light, low power consumption, wide viewing angle, high contrast, simple fabrication methods and rapid response time.

The first observation of electroluminescence in organic materials were in the early 1950s by Andre Bernanose and co-workers at the Nancy-University in France. Martin Pope and his co-workers at New York University first observed direct current (DC) electroluminescence on a single pure crystal of anthracene and on anthracene crystals doped with tetracene under vacuum in 1963.

The first diode device was reported by Ching W. Tang and Steven Van Slyke at Eastman Kodak in 1987. The device used a two-layer structure with separate hole transporting and electron transporting layers resulted in reduction in operating voltage and improvement of the efficiency, that led to the current era of organic EL research and device production.

Typically organic EL device is composed of layers of organic materials situated between two electrodes, which include a hole transporting layer (HTL), an emitting layer (EML), an electron transporting layer (ETL). The basic mechanism of organic EL involves the injection of the carrier, transport, recombination of carriers and exciton formed to emit light. When an external voltage is applied to an organic EL device, electrons and holes are injected from a cathode and an anode, respectively, electrons will be injected from a cathode into a LUMO (lowest unoccupied molecular orbital) and holes will be injected from an anode into a HOMO (highest occupied molecular orbital). When the electrons recombine with holes in the emitting layer, excitons are formed and then emit light. When luminescent molecules absorb energy to achieve an excited state, an exciton may either be in a singlet state or a triplet state depending on how the spins of the electron and hole have been combined. 75% of the excitons form by recombination of electrons and holes to achieve a triplet excited state. Decay from triplet states is spin forbidden, Thus, a fluorescence electroluminescent device has only 25% internal quantum efficiency. In contrast to fluorescence electroluminescent device, phosphorescent organic EL device make use of spin-orbit interactions to facilitate intersystem crossing between singlet and triplet states, thus obtaining emission from both singlet and triplet states and the internal quantum efficiency of electroluminescent devices from 25% to 100%.

Recently, a new type of fluorescent organic EL device incorporating mechanism of thermally activated delayed fluorescence (TADF) has been developed by Adachi and coworkers is a promising way to obtain a high efficiency of exciton formation by converting spin-forbidden triplet excitons up to the siglet level by the mechanism of reverse intersystem crossing (RISC).

The organic EL utilizes both triplet and singlet excitons. Cause of longer lifetime and the diffusion length of triplet excitons compared to those of singlet excitons, the phosphorescent organic EL generally need an additional hole blocking layer (HBL) between the emitting layer (EML) and the electron transporting layer (ETL) or electron blocking layer (EBL) between the emitting layer (EML) and the hole transporting layer (HTL). The purpose of the use of HBL or EBL is to confine the recombination of injected holes and electrons and the relaxation of created excitons within the EML, hence the device's efficiency can be improved. To meet such roles, the hole blocking materials or electron blocking materials must have HOMO (highest occupied molecular orbital) and LUMO (lowest unoccupied molecular orbital) energy levels suitable to block hole or electron transport from the EML to the ETL or the HTL.

There continues to be a need for organic EL materials which is able to efficiently transport electrons or holes and block electrons or holes, with good thermal stability, and more efficient hole transport material (HTM) and electron blocking material (EBM) that can lower driving voltage and power consumption, increasing efficiency and half-life time. According to the reasons described above, the present invention has the objective of resolving such problems of the prior-art like as EP2313362A1, US20130048975A1, WO20080672636A1, WO2012091471A2. In the present invention we used the indenotriphenylene core link to diaryldiamine group or heteroaryldiamine group to finish the novel derivative represented as general formula (1) and offering a light emitting device which is excellent in its thermal stability, high luminance efficiency, high luminance and long half-life time to improve the prior materials and the prior organic EL device. Indenotriphenylene skeleton based derivative disclosed in JP2013232520, KR20120072784, WO2008062636, WO2012091471, U.S. Pat. No. 8,962,160B2, U.S. Pat. No. 8,993,130B2, 20140231754A1 US20140151645A1, US20130048975A1, 20140175383A1 and US20140209866A1 are used for organic EL device are described. There are no prior arts demonstrate an indenotriphenylene-based diamine skeleton used as hole transport material, electron blocking material and fluorescent emitting dopant for organic EL device.

According to the reasons described above, the present invention has the objective of resolving such problems of the prior-art and offering a light emitting device which is excellent in its thermal stability, high luminance efficiency, high luminance and long half-life time. The present invention disclose an indenotriphenylene-based diamine derivative having general formula (1), used as hole transport layer, electron blocking layer and fluorescent emitting dopant of emitting layer have good charge carrier mobility and excellent operational durability can lower driving voltage and power consumption, increasing efficiency and half-life time of organic EL device.

SUMMARY OF THE INVENTION

In accordance with the present invention, the indenotriphenylene-based diamine derivative and their use for hole transport layer, electron blocking layer and fluorescent emitting dopant of emitting layer for organic EL device are provided. The derivative can overcome the drawbacks of the conventional materials like as shorter half-life time, lower efficiency, higher driving voltage.

The present invention has the economic advantages for industrial practice. Accordingly, the present invention discloses the indenotriphenylene-based diamine derivative which can be used for organic EL device is disclosed. The mentioned the indenotriphenylene-based diamine derivative is represented by the following formula (1):

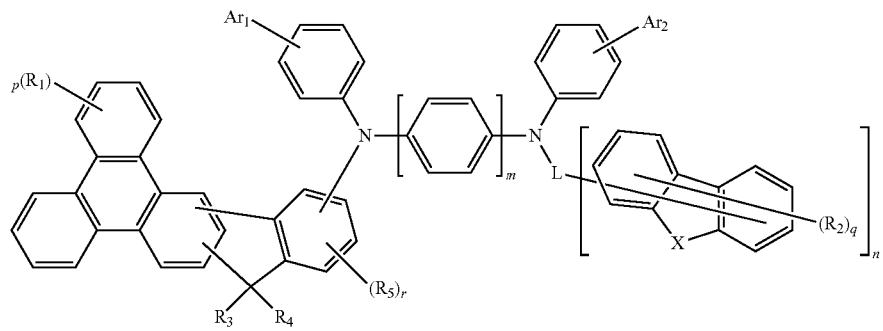

formula (1)

wherein $Ar_1$ and $Ar_2$ represent a hydrogen atom and a substituted or unsubstituted non-fused aryl group having 6~20 carbon atoms, m represent an integer of 0 to 4, r represent an integer of 0 to 3, p and q represent an integer of 0 to 8, n represents an integer of 0 or 1; when n represents an integer of 0, L represents a substituted or unsubstituted divalent arylene group having 6 to 30 carbon atoms, when n represents an integer of 1, L represents a single bond and a substituted or unsubstituted divalent arylene group having 6 to 30 carbon atoms, X represents a divalent bridge selected from the atom or group consisting from O, S, $C(R_6)(R_7)$ and $N(R_8)$, $R_1$ to $R_8$ are independently selected from the group consisting of a hydrogen atom, a substituted or unsubstituted alkyl group having 1 to 20 carbon atoms, a substituted or unsubstituted aryl group having 6 to 30 carbon atoms and a substituted or unsubstituted heteroaryl group having 3 to 30 carbon atoms.

BRIEF DESCRIPTION OF THE DRAWINGS

FIG. 1 show one example of organic EL device in the present invention, wherein 6 is transparent electrode, 14 is metal electrode, 7 is hole injection layer which is deposited onto 6, 8 is hole transport layer which is deposited onto 7, 9 is electron blocking layer which is deposited onto 8, 10 is fluorescent or phosphorescent emitting layer which is deposited onto 9, 11 is hole blocking layer which is deposited onto 10, 12 is electron transport layer which is deposited on to 11, and 13 is electron injection layer which is deposited on to 12.

DESCRIPTION OF THE PREFERRED EMBODIMENTS

What probed into the invention is the indenotriphenylene-based diamine derivative and organic EL device using the derivative. Detailed descriptions of the production, structure and elements will be provided in the following to make the invention thoroughly understood. Obviously, the application of the invention is not confined to specific details familiar to those who are skilled in the art. On the other hand, the common elements and procedures that are known to everyone are not described in details to avoid unnecessary limits of the invention. Some preferred embodiments of the present invention will now be described in greater detail in the following. However, it should be recognized that the present invention can be practiced in a wide range of other embodiments besides those explicitly described, that is, this invention can also be applied extensively to other embodiments, and the scope of the present invention is expressly not limited except as specified in the accompanying claims In a first embodiment of the present invention, the indenotriphenylene-based diamine derivative which can be used as hole transport layer, electron blocking layer and fluorescent emitting dopant of emitting layer for organic EL device are disclosed. The mentioned the indenotriphenylene-based diamine derivative represented by the following formula (1):

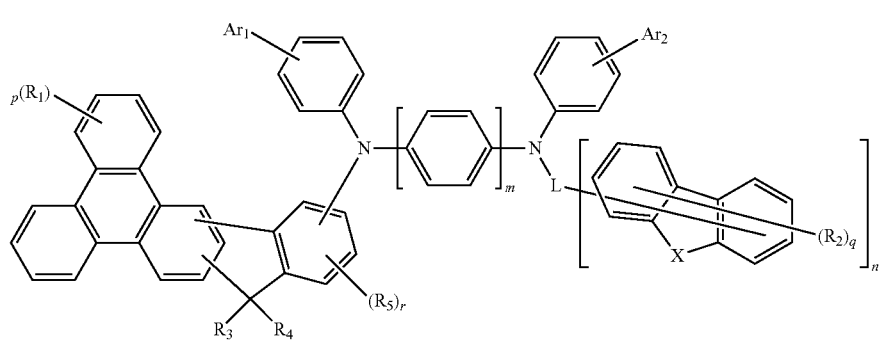

formula (1)

wherein $Ar_1$ and $Ar_2$ represent a hydrogen atom and a substituted or unsubstituted non-fused aryl group having 6~20 carbon atoms, m represent an integer of 0 to 4, r represent an integer of 0 to 3, p and q represent an integer of 0 to 8, n represents an integer of 0 or 1; when n represents an integer of 0, L represents a substituted or unsubstituted divalent arylene group having 6 to 30 carbon atoms, when n represents an integer of 1, L represents a single bond and a substituted or unsubstituted divalent arylene group having 6 to 30 carbon atoms, X represents a divalent bridge selected from the atom or group consisting from O, S, $C(R_6)(R_7)$ and $N(R_8)$, $R_1$ to $R_8$ are independently selected from the group consisting of a hydrogen atom, a substituted or unsubstituted alkyl group having 1 to 20 carbon atoms, a substituted or unsubstituted aryl group having 6 to 30 carbon atoms and a substituted or unsubstituted heteroaryl group having 3 to 30 carbon atoms.

According to the above-mentioned the indenotriphenylene-based diamine derivative formula (1) represented by the following formula (2) to formula (4):

wherein $Ar_1$ and $Ar_2$ represent a hydrogen atom and a substituted or unsubstituted non-fused aryl group having 6~20 carbon atoms, m represent an integer of 0 to 4, r represent an integer of 0 to 3, p and q represent an integer of 0 to 8, n represents an integer of 0 or 1; when n represents an integer of 0, L represents a substituted or unsubstituted divalent arylene group having 6 to 30 carbon atoms, when n represents an integer of 1, L represents a single bond and a substituted or unsubstituted divalent arylene group having 6 to 30 carbon atoms, X represents a divalent bridge selected from the atom or group consisting from O, S, $C(R_6)(R_7)$ and $N(R_8)$, $R_1$ to $R_8$ are independently selected from the group consisting of a hydrogen atom, a substituted or unsubstituted alkyl group having 1 to 20 carbon atoms, a substituted or unsubstituted aryl group having 6 to 30 carbon atoms and a substituted or unsubstituted heteroaryl group having 3 to 30 carbon atoms.

According to the above-mentioned the indenotriphenylene-based diamine derivative formula (2) to formula (4), when m represents an integer of 2, n represents an integer of 1, L represents a single bond or a substituted or unsubstituted phenylene group, preferably the indenotriph-

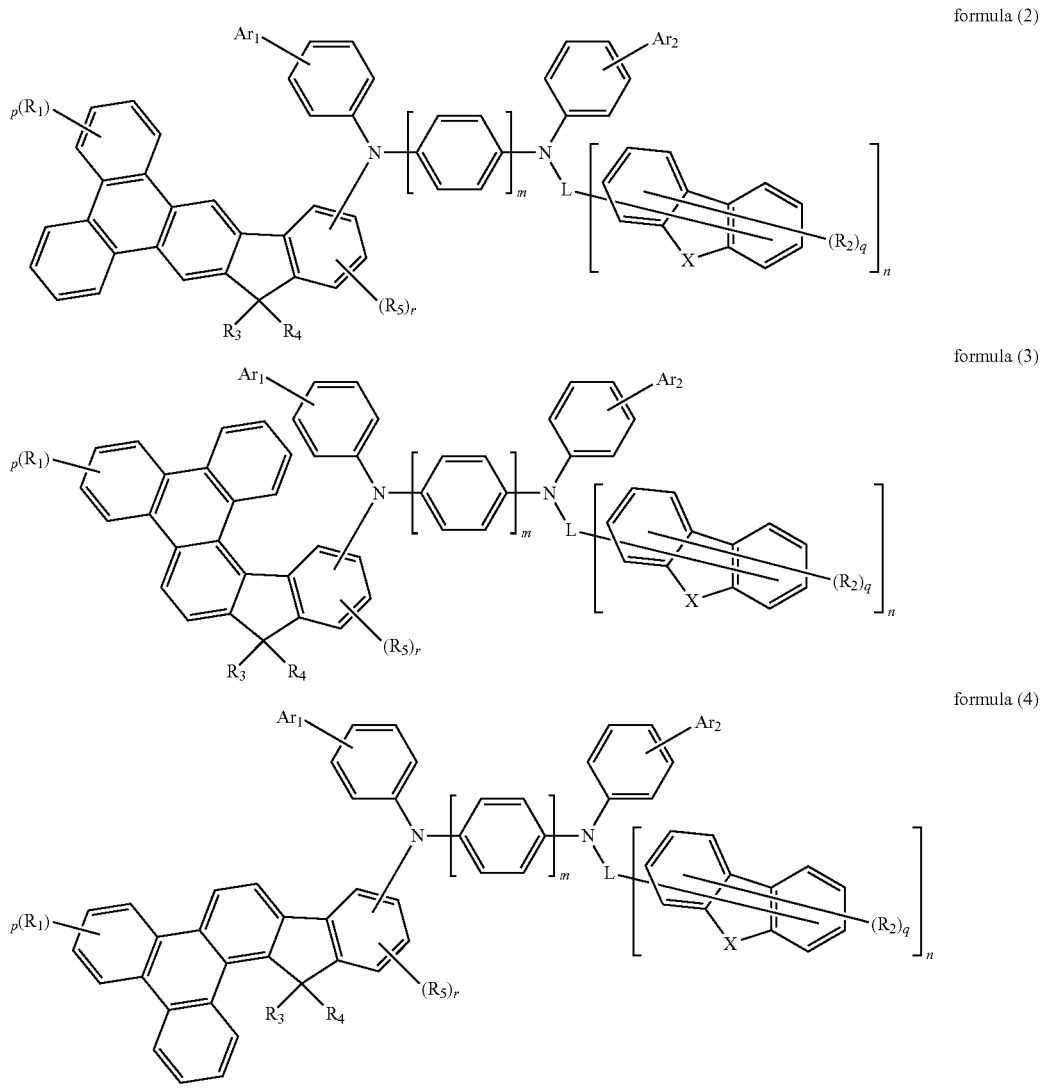

formula (2)

formula (3)

formula (4)

enylene-based diamine derivative formula (2) to formula (4) are represented by the following formula (5) to formula (10):

formula(5)
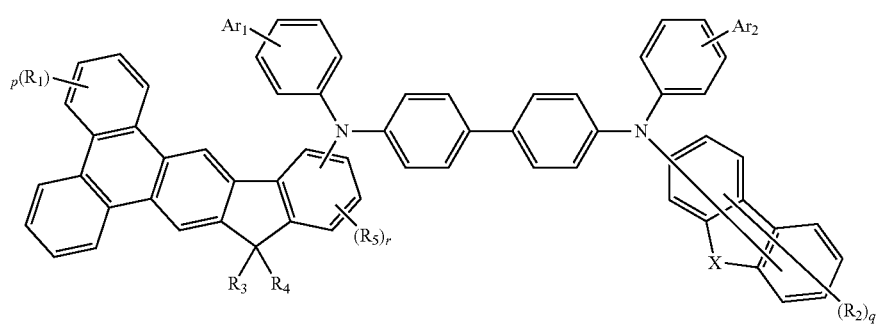
formula(6)
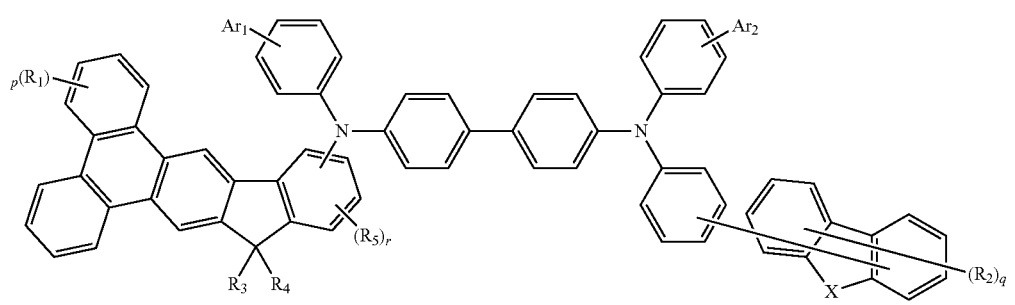
formula(7)
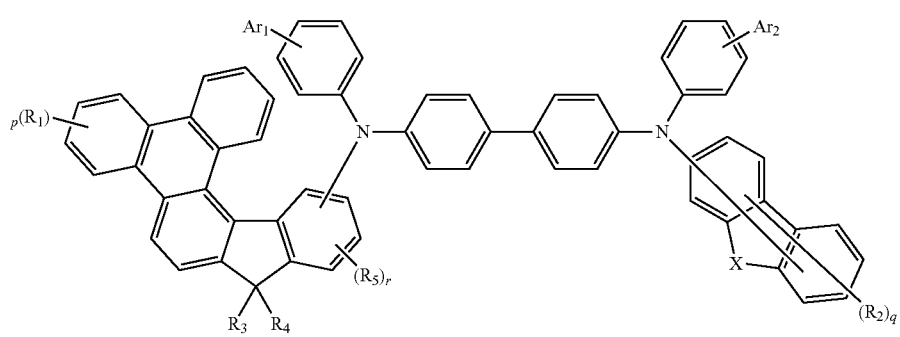
formula(8)
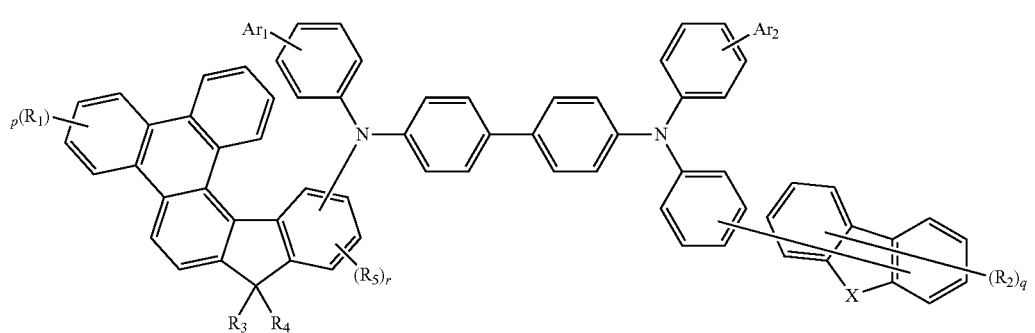
formula(9)
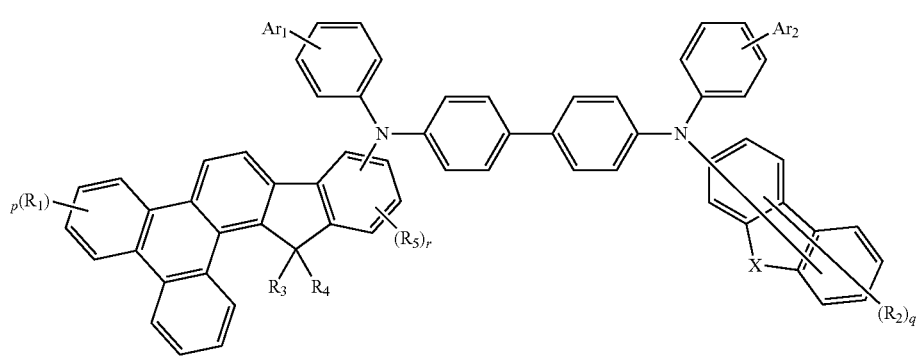

-continued

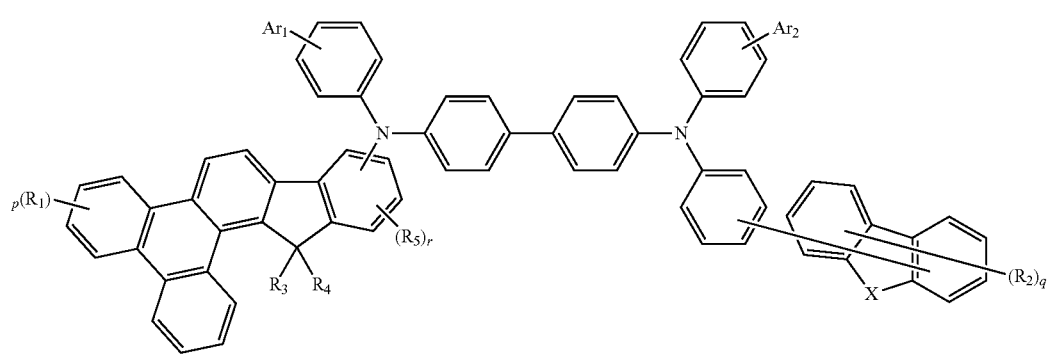

formula(10)

wherein $Ar_1$ and $Ar_2$ represent a hydrogen atom and a substituted or unsubstituted non-fused aryl group having 6~20 carbon atoms, r represent an integer of 0 to 3, p and q represent an integer of 0 to 8, X represents a divalent bridge selected from the atom or group consisting from O, S, $C(R_6)(R_7)$ and $N(R_8)$, $R_1$ to $R_8$ are independently selected from the group consisting of a hydrogen atom, a substituted or unsubstituted alkyl group having 1 to 20 carbon atoms, a substituted or unsubstituted aryl group having 6 to 30 carbon atoms and a substituted or unsubstituted heteroaryl group having 3 to 30 carbon atoms.

According to the above-mentioned the indenotriphenylene-based diamine derivative formula (5) to formula (10), wherein $Ar_1$ and $Ar_2$ are represented by the following formulas:

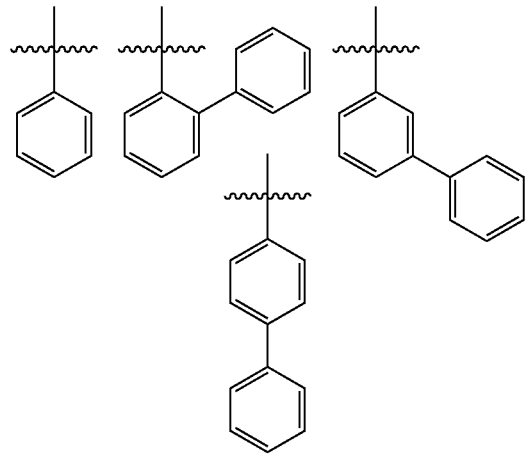

In this embodiment, some organic material are shown below:

EX1

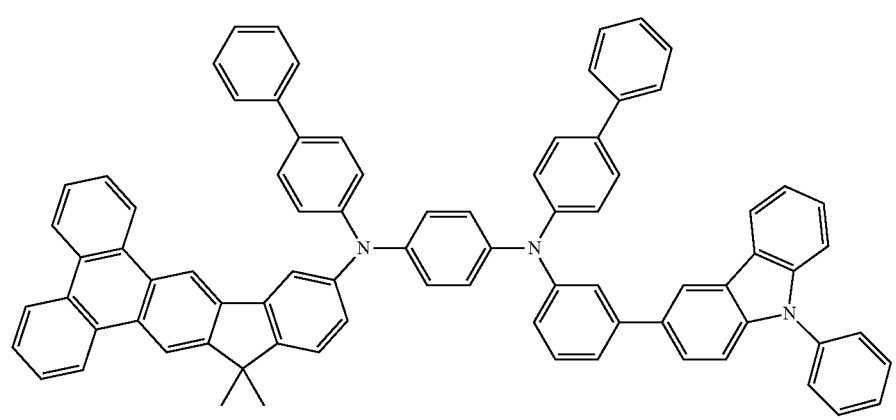

EX2
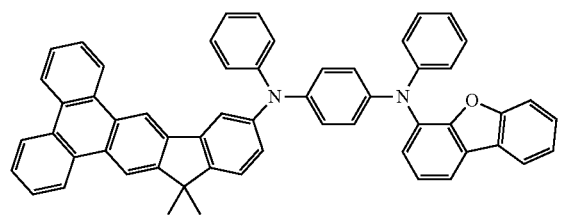
EX3
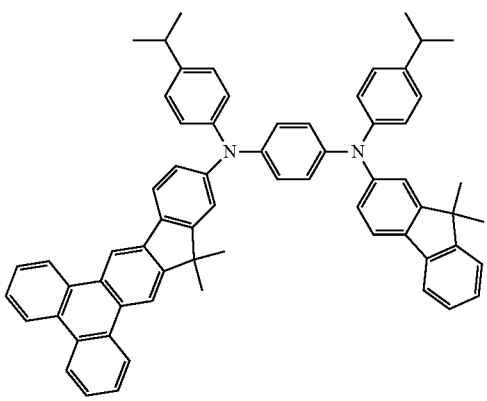
EX4
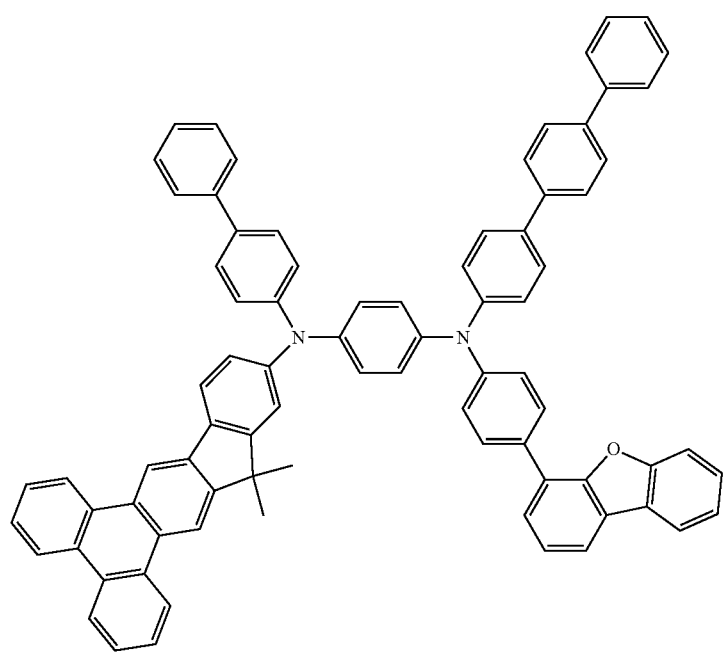
EX5
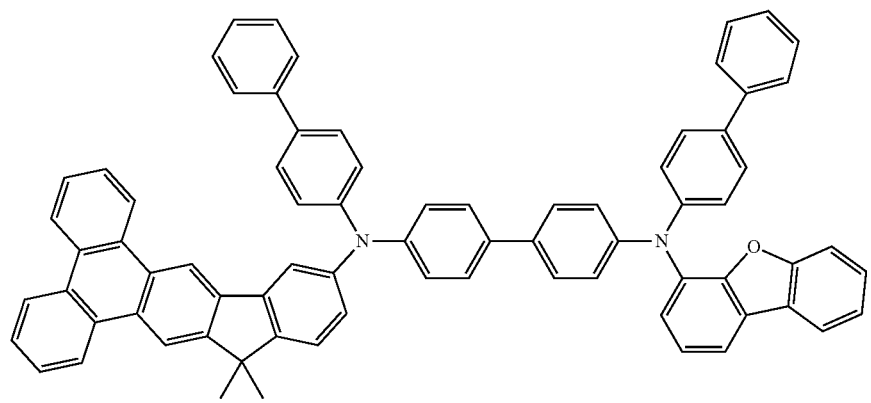

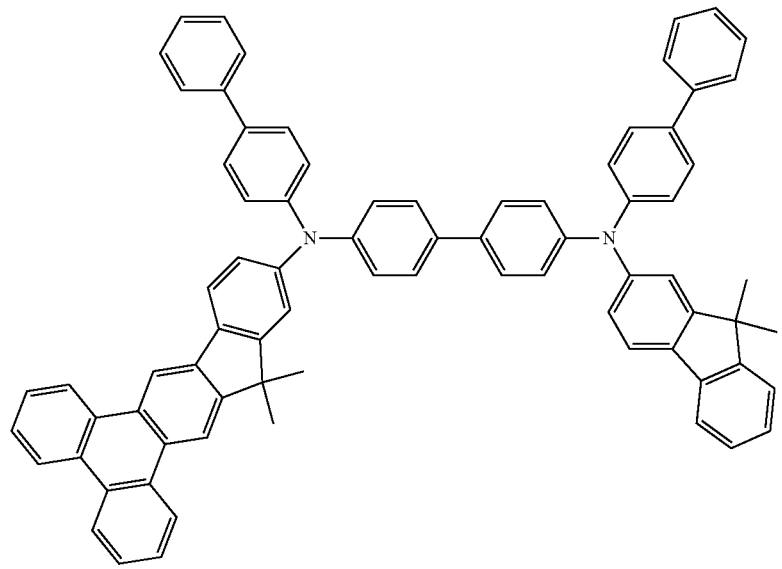
EX6
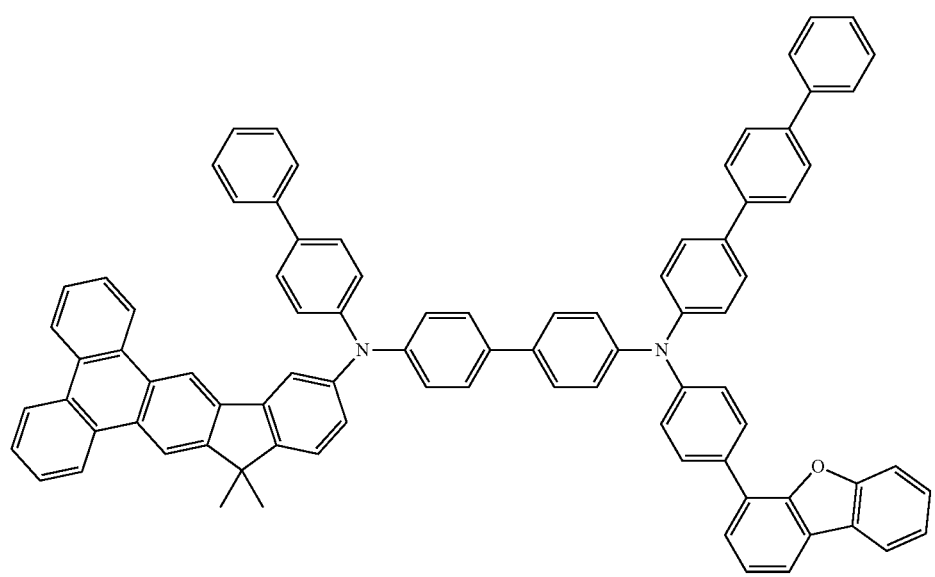
EX7
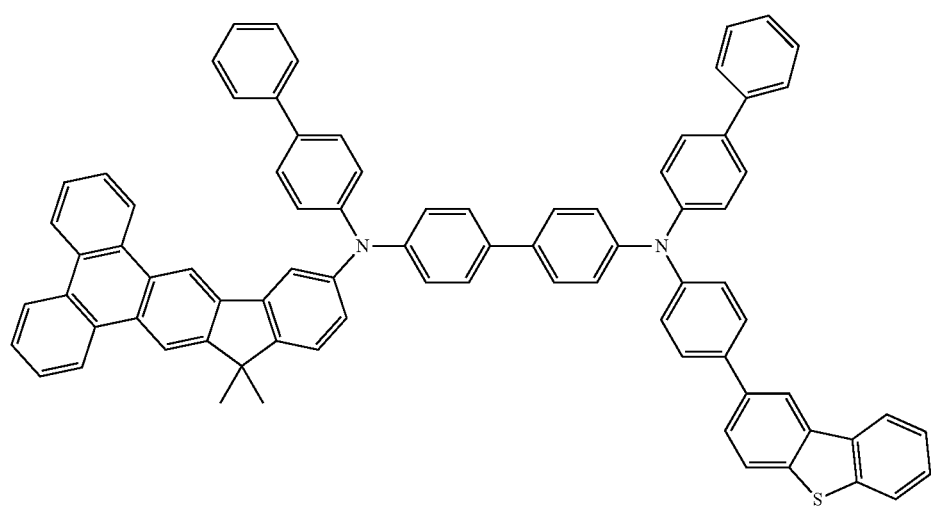
EX8

-continued
EX9
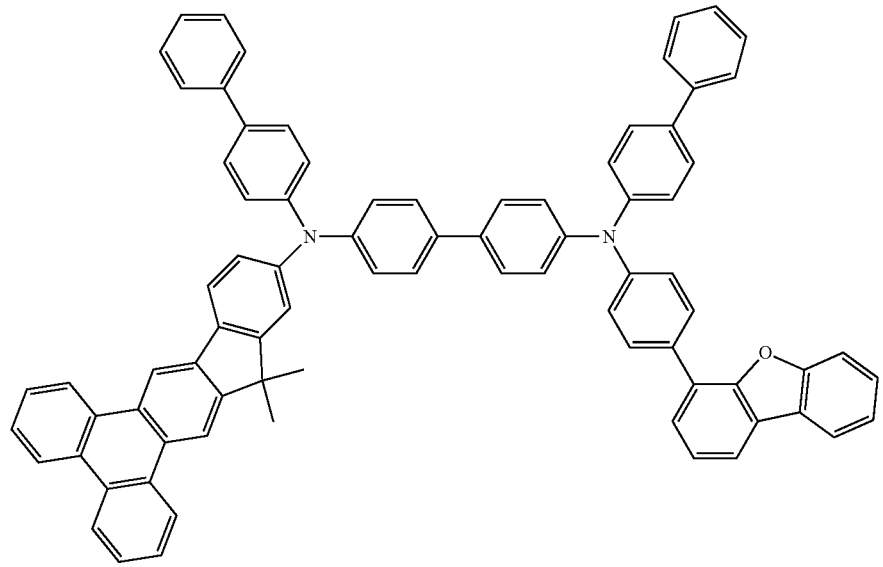
EX10
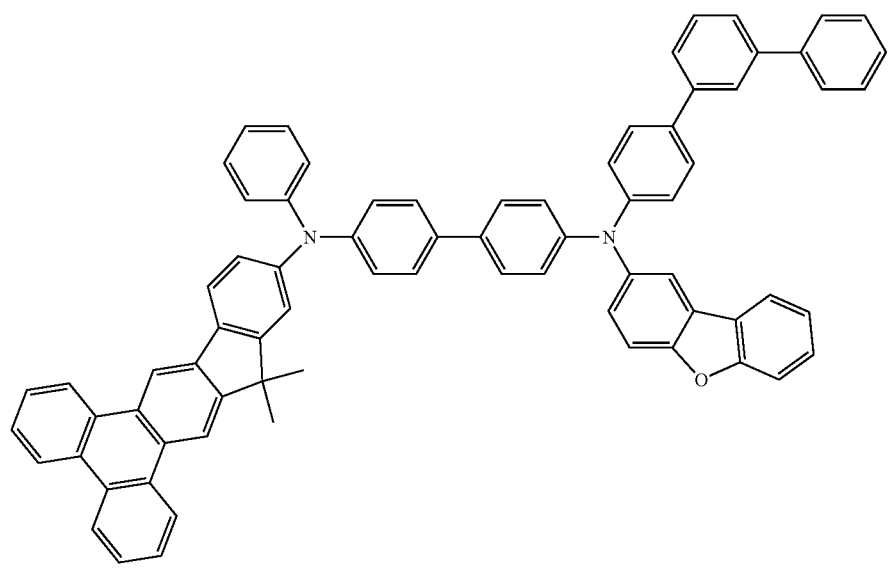
EX11
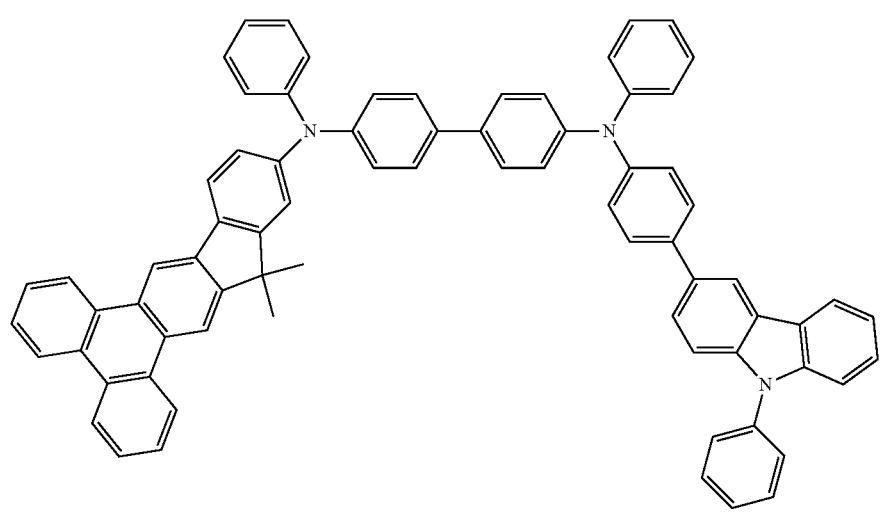

EX12
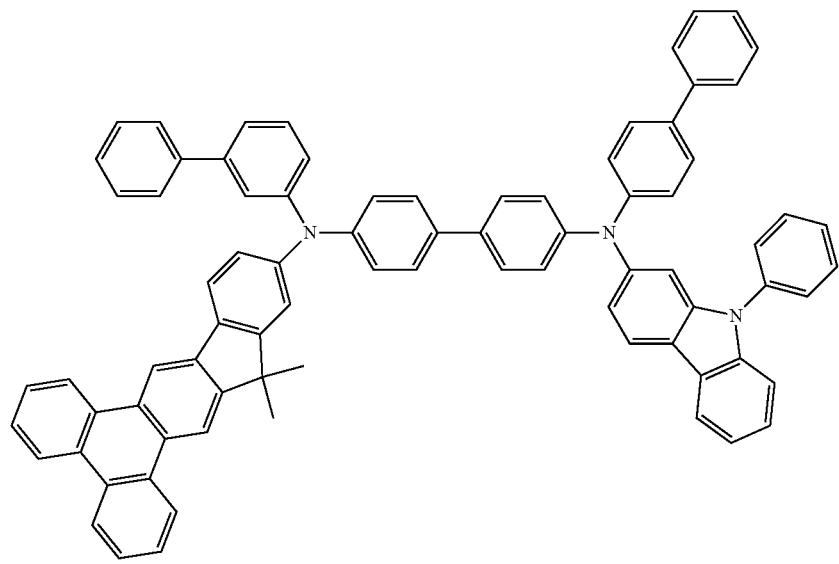
EX13
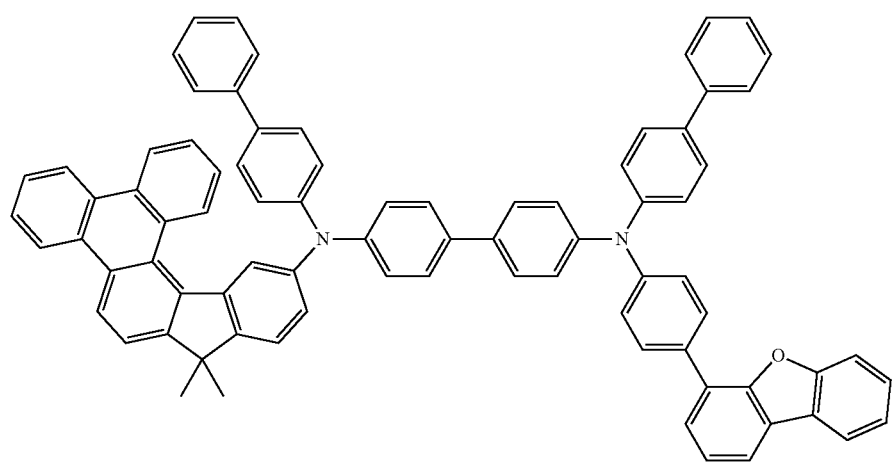
EX14
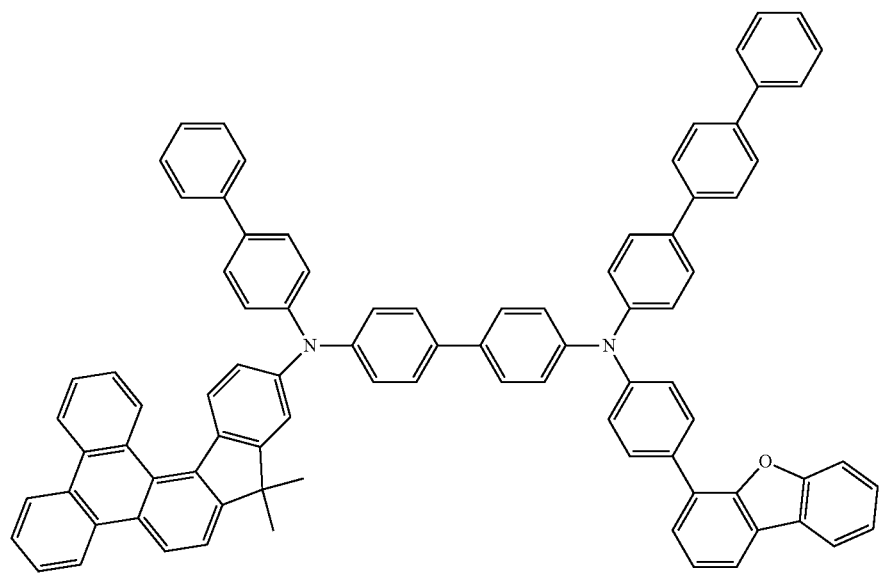

-continued
EX15
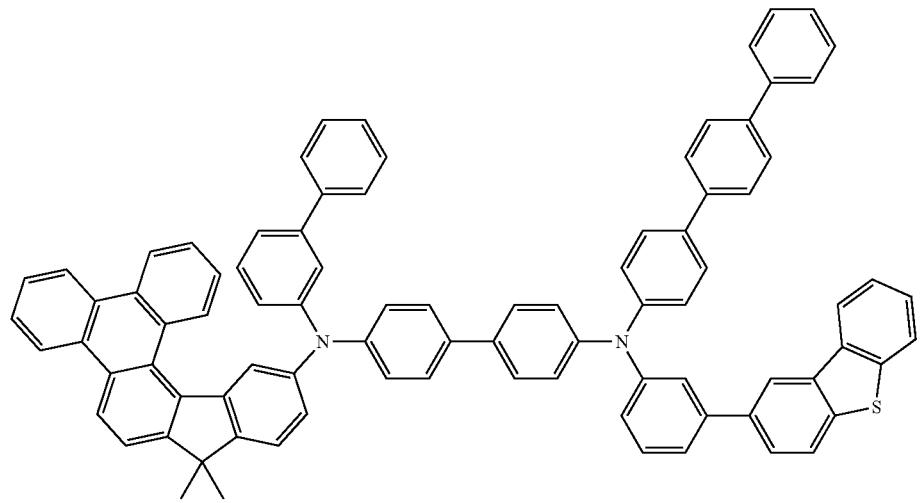
EX16
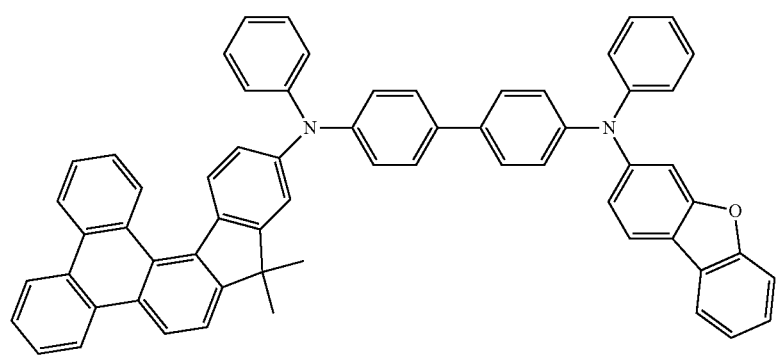
EX17
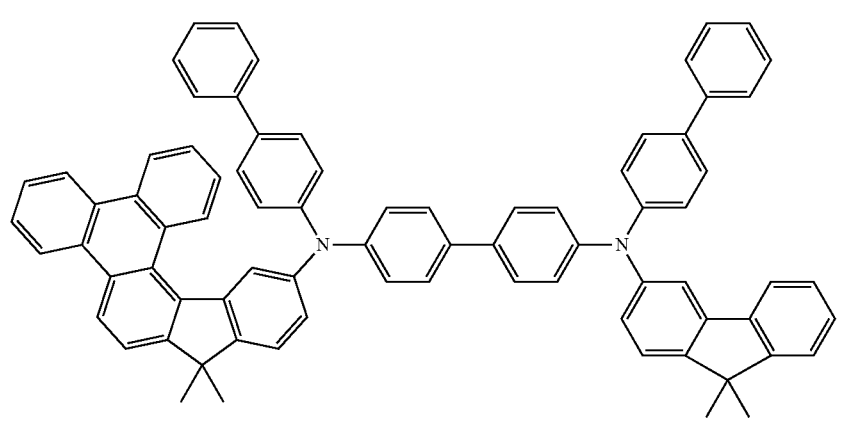

EX18
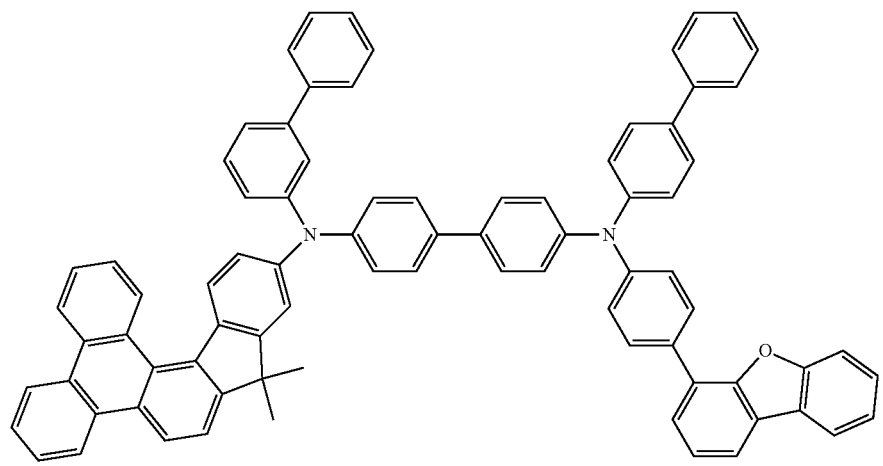
EX19
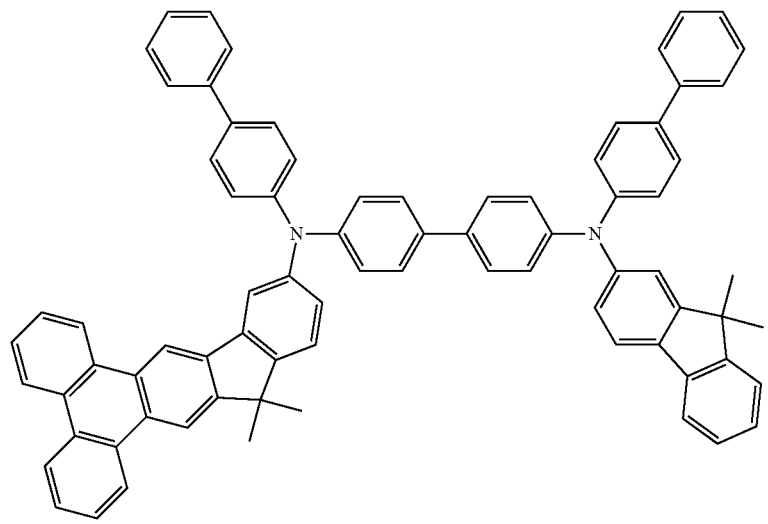
EX20
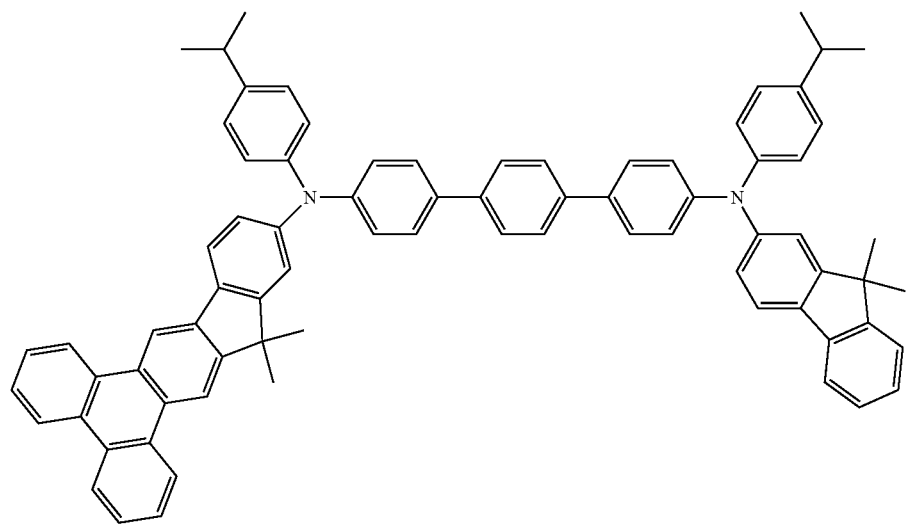

-continued
EX21
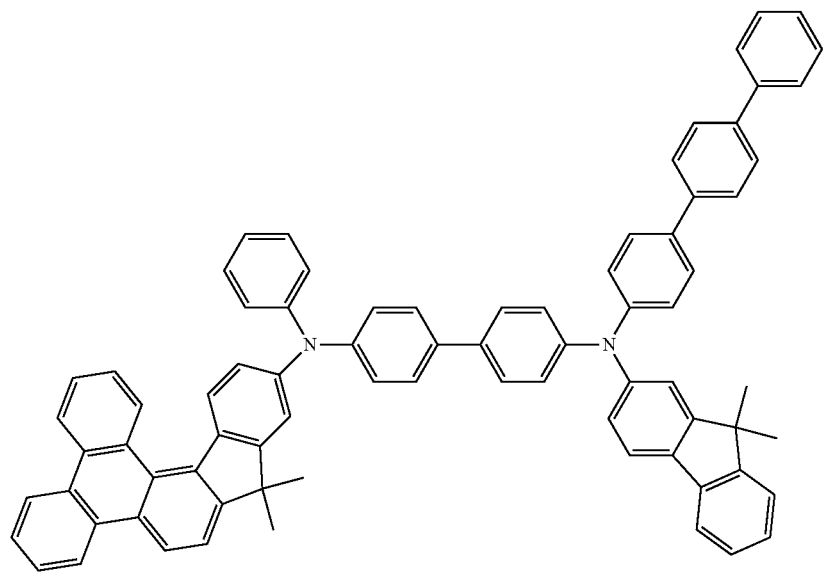
EX22
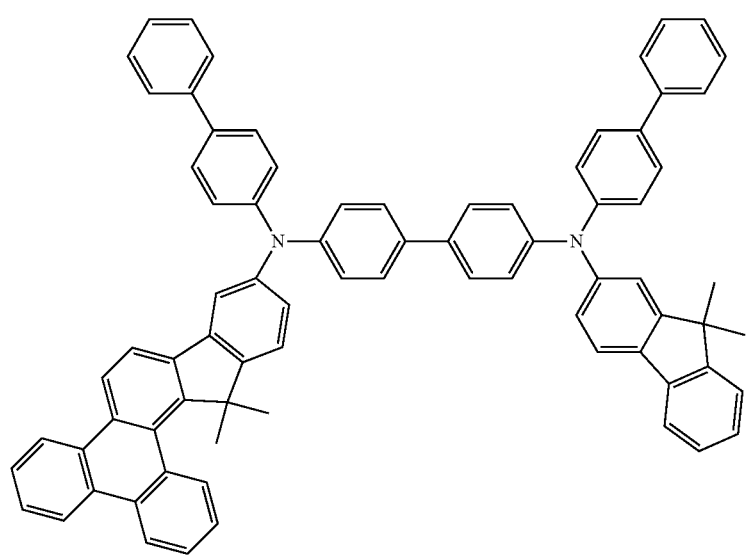
EX23
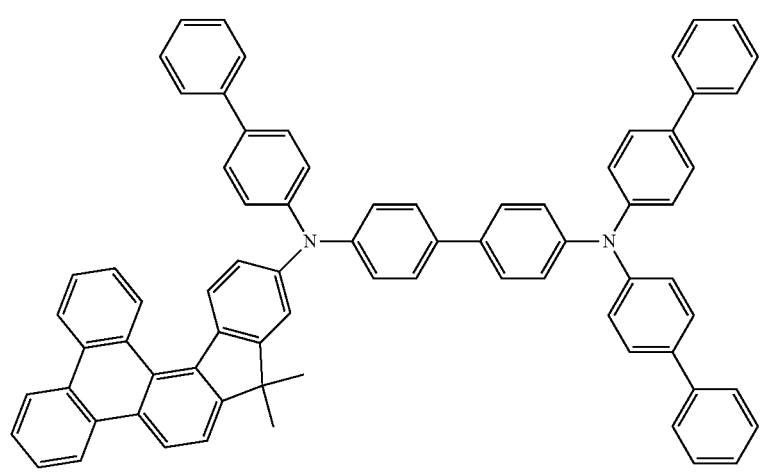

-continued
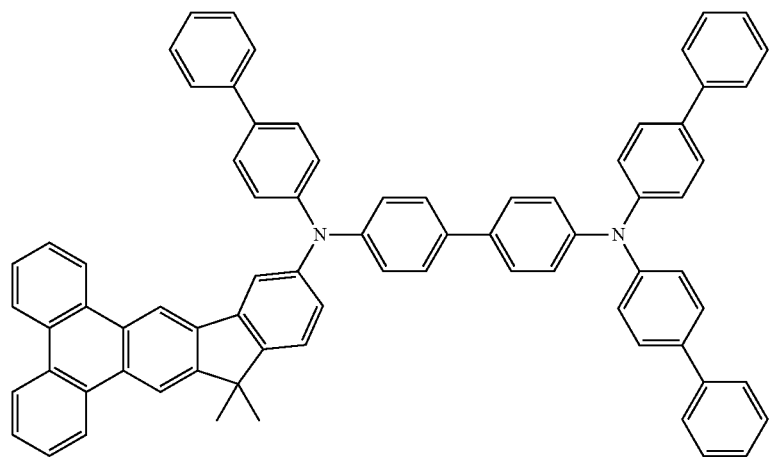
EX24
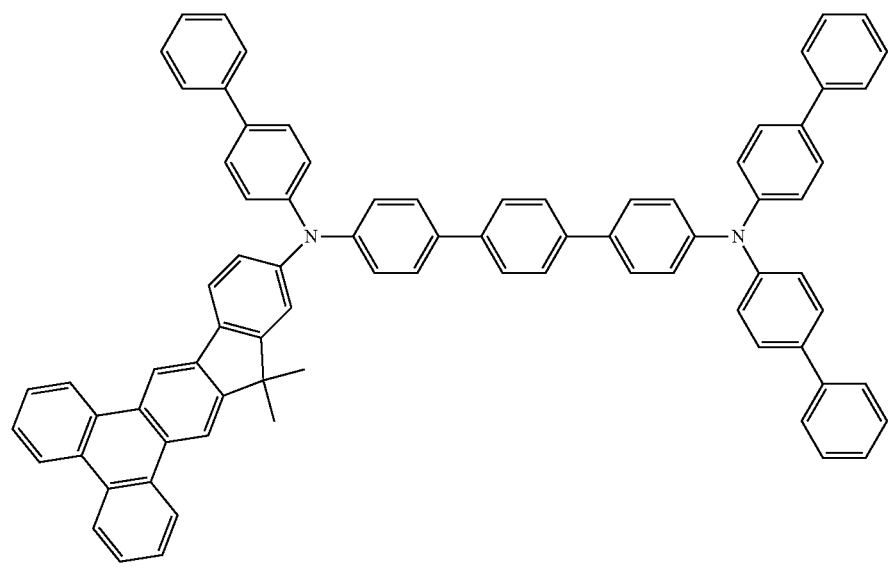
EX25
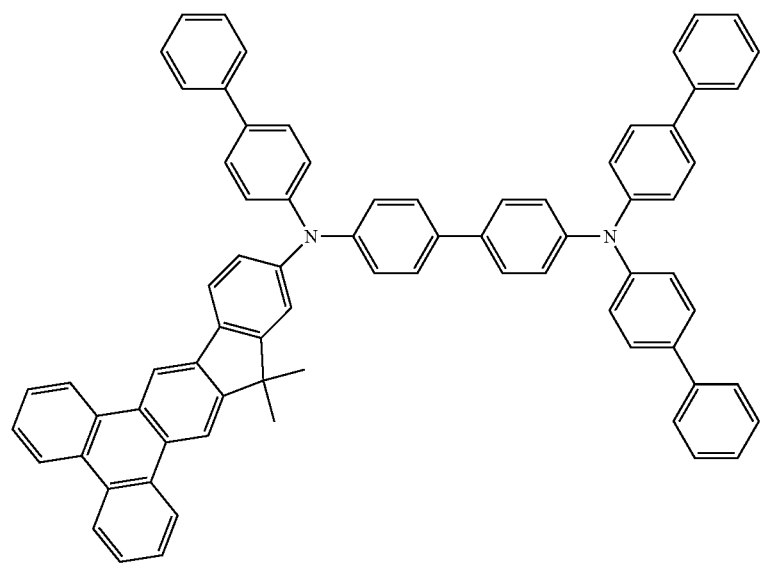
EX26
Detailed preparation for the indenotriphenylene-based diamine derivative present invention could be clarified by exemplary embodiments, but the present invention is not limited to exemplary embodiments. EXAMPLE 1 and EXAMPLE 2 show the preparation for examples of the derivative in the present invention. EXAMPLE 3 shows the fabrication of organic EL device and I-V-B, half-life time of organic EL device testing report.

Example 1

Synthesis of EX9

Synthesis of N$^4$,N$^{4'}$-di(biphenyl-4-yl)-N$^4$-(10,10-dimethyl-10H-indeno[2,1-b]triphenylen-12-yl)biphenyl-4,4'-diamine

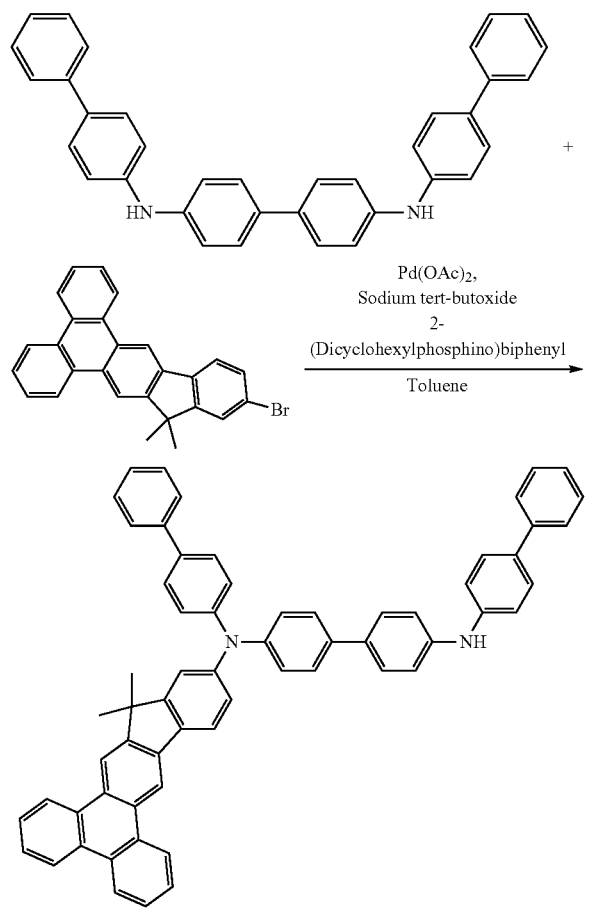

Synthesis of N$^4$,N$^{4'}$-di(biphenyl-4-yl)-N$^4$-(4-(dibenzo[b,d]furan-4-yl)phenyl)-N$^{4'}$-(10,10-dimethyl-10H-indeno[2,1-b]triphenylen-12-yl)biphenyl-4,4'-diamine

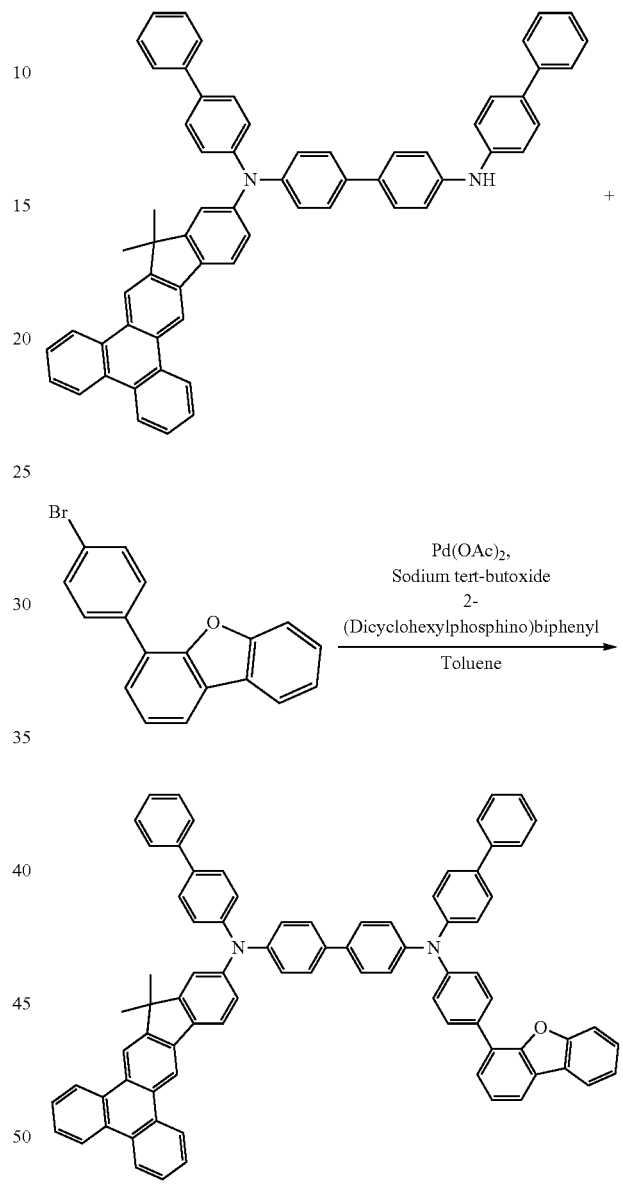

A mixture of 4.5 g (9.3 mmol) N$^4$,N$^{4'}$-di(biphenyl-4-yl) biphenyl-4,4'-diamine, 2.2 g (10.0 mmol) of 12-bromo-10,10-dimethyl-10H-indeno [1,2-b]triphenylene, 0.05 g (0.2 mmol) of palladium(II)acetate, 0.13 g (0.38 mmol) of 2-(dicyclohexylphosphino)biphenyl, 1.3 g (14 mmol) of sodium tert-butoxide and 100 ml of toluene was refluxed under nitrogen overnight. After finishing the reaction, then cooled to room temperature. The organic layer was extracted with dichloromethane and water, dried with anhydrous magnesium sulfate, the solvent was removed and the residue was purified by column chromatography on silica gel (hexane-dichloromethane) to give product 3.6 g (yield 47%) as a yellow solid.

A mixture of 3.6 g (4.3 mmol) N$^4$,N$^{4'}$-di(biphenyl-4-yl)-N$^4$-(10,10-dimethyl-10H-indeno[2,1-b]triphenylen-12-yl) biphenyl-4,4'-diamine, 1.6 g (5.0 mmol) of 4-(4-bromophenyl)dibenzo[b,d]furan, 0.025 g (0.1 mmol) of palladium(II) acetate, 0.07 g (0.19 mmol) of 2-(dicyclohexylphosphino) biphenyl, 0.65 g (7 mmol) of sodium tert-butoxide and 50 ml of toluene was refluxed under nitrogen overnight. After finishing the reaction, then cooled to room temperature. The organic layer was extracted with dichloromethane and water, dried with anhydrous magnesium sulfate, the solvent was removed and the residue was purified by column chromatography on silica gel (hexane-dichloromethane) to give product 2.8 g (yield 61%) as a yellow solid. MS (m/z, FAB$^+$): 1072.1

Example 2

Synthesis of EX26

Synthesis of N⁴,N⁴,N⁴'-tri(biphenyl-4-yl)-N⁴'-(10,10-dimethyl-10H-indeno[2,1-b]triphenylen-12-yl)biphenyl-4,4'-diamine

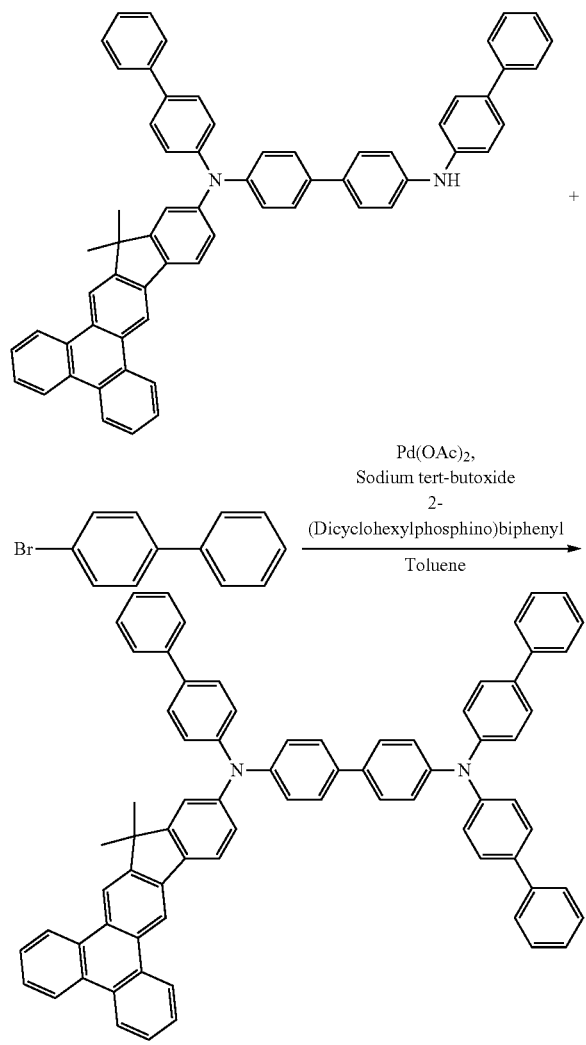

A mixture of 3.6 g (4.3 mmol) $N^4,N^{4'}$-di(biphenyl-4-yl)-$N^4$-(10,10-dimethyl-10H-indeno[2,1-b]triphenylen-12-yl)biphenyl-4,4'-diamine, 1.2 g (5.0 mmol) of 4-bromobiphenyl, 0.025 g (0.1 mmol) of palladium(II)acetate, 0.07 g (0.19 mmol) of 2-(dicyclohexylphosphino)biphenyl, 0.65 g (7 mmol) of sodium tert-butoxide and 50 ml of toluene was refluxed under nitrogen overnight. After finishing the reaction, then cooled to room temperature. The organic layer was extracted with dichloromethane and water, dried with anhydrous magnesium sulfate, the solvent was removed and the residue was purified by column chromatography on silica gel (hexane-dichloromethane) to give product 2.3 g (yield 54%) as a yellow solid. MS (m/z, FAB⁺): 982.6

General Method of Producing Organic EL Device

ITO-coated glasses with 9~12 ohm/square in resistance and 120~160 nm in thickness are provided (hereinafter ITO substrate) and cleaned in a number of cleaning steps in an ultrasonic bath (e.g. detergent, deionized water). Before vapor deposition of the organic layers, cleaned ITO substrates are further treated by UV and ozone. All pre-treatment processes for ITO substrate are under clean room (class 100).

These organic layers are applied onto the ITO substrate in order by vapor deposition in a high-vacuum unit ($10^{-7}$ Torr), such as: resistively heated quartz boats. The thickness of the respective layer and the vapor deposition rate (0.1~0.3 nm/sec) are precisely monitored or set with the aid of a quartz-crystal monitor. It is also possible, as described above, for individual layers to consist of more than one compound, i.e. in general a host material doped with a dopant material. This is achieved by co-vaporization from two or more sources.

Dipyrazino[2,3-f:2,3-]quinoxaline-2,3,6,7,10,11-hexacarbonitrile (HAT-CN) is used as hole injection layer in this organic EL device, N,N-Bis (naphthalene-1-yl)-N,N-bis(phenyl)-benzidine (NPB) is most widely used as the hole transporting layer used for comparison; 10,10-dimethyl-12-(10-(4-(naphthalene-1-yl)phenyl)anthracen-9-yl)-10H-indeno[2,1-b]triphenylene (H3) is used as emitting host in organic EL device and N1,N1,N6,N6-tetram-tolylpyrene-1,6-diamine (D1) is used as blue dopant for comparison; HB3 (see the following chemical structure) is used as hole blocking material (HBM) and 2-(naphthalen-1-yl)-9-(4-(1-(4-(10-naphthalene-2-yl)anthracen-9-yl)phenyl)-1H-benzo[d]imidazol-2-yl)phenyl)-1,10-phenanthroline (ET2) is used as electron transporting material to co-deposit with 8-hydroxyquinolato-lithium (LiQ) in organic EL device. The prior art of OLED materials for producing standard organic EL device control and comparable material in this invention shown its chemical structure as follows:

-continued
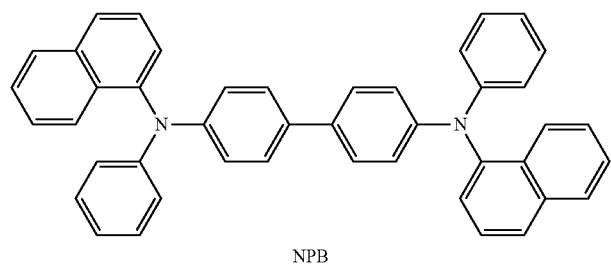
NPB
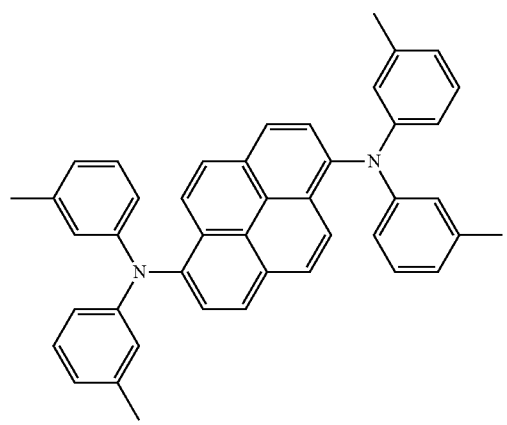
D1
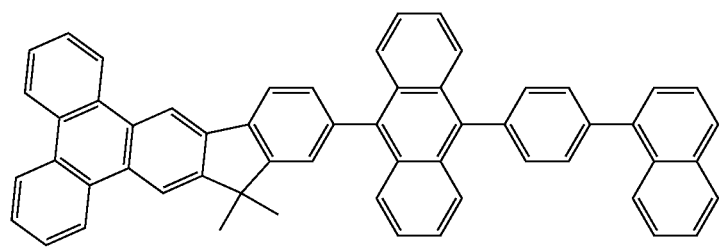
H3
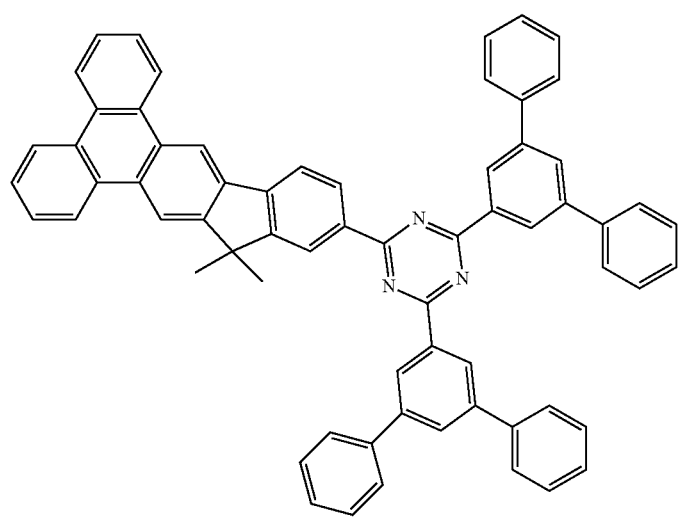
HB3
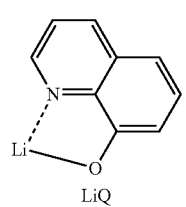
LiQ -continued
ET2
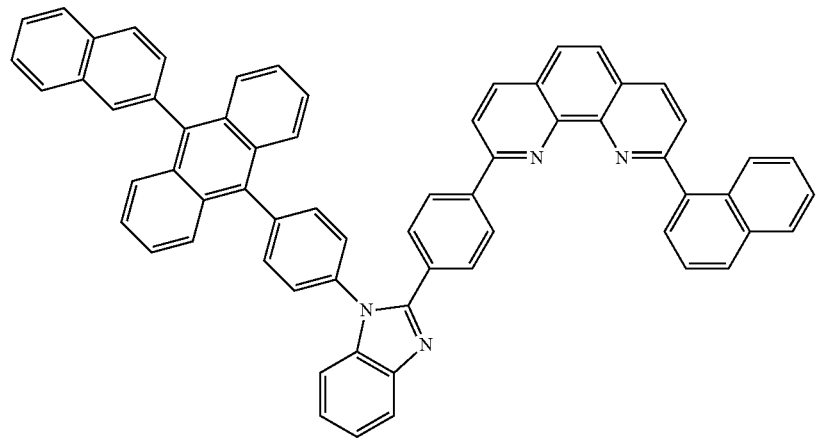
EX3
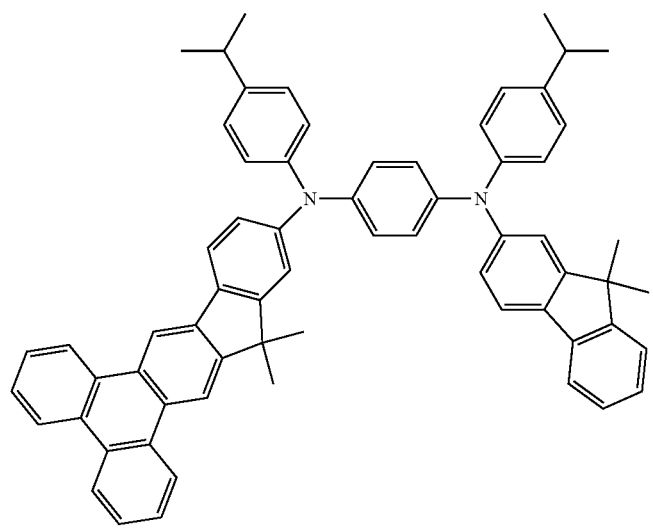
EX9
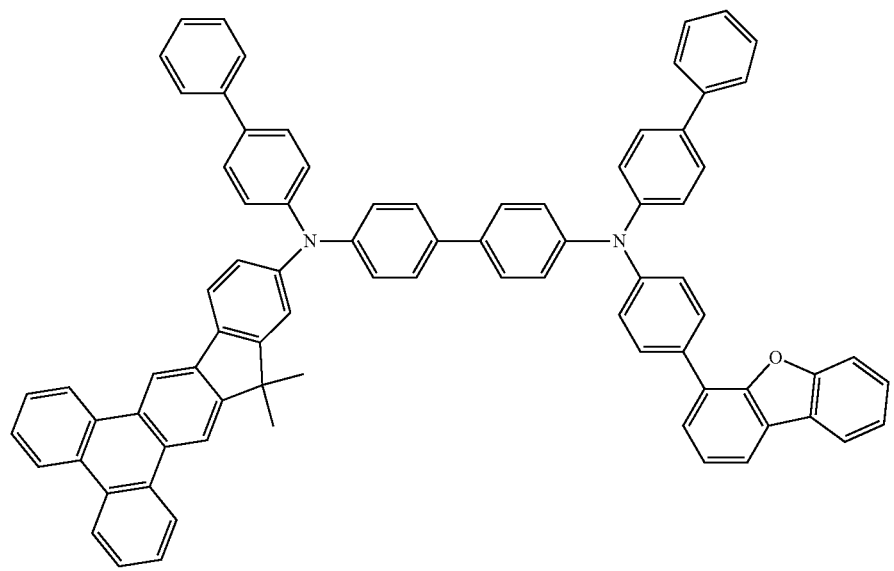

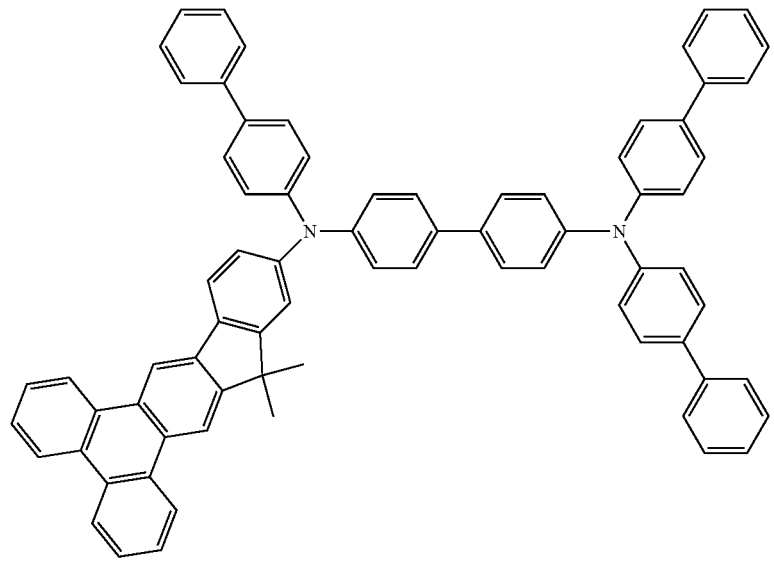

EX26

A typical organic EL device consists of low work function metals, such as Al, Mg, Ca, Li and K, as the cathode by thermal evaporation, and the low work function metals can help electrons injecting the electron transporting layer from cathode. In addition, for reducing the electron injection barrier and improving the organic EL device performance, a thin-film electron injecting layer is introduced between the cathode and the electron transporting layer. Conventional materials of electron injecting layer are metal halide or metal oxide with low work function, such as: LiF, LiQ, MgO, or $Li_2O$. On the other hand, after the organic EL device fabrication, EL spectra and CIE coordination are measured by using a PR650 spectra scan spectrometer. Furthermore, the current/voltage, luminescence/voltage and yield/voltage characteristics are taken with a Keithley 2400 programmable voltage-current source. The above-mentioned apparatuses are operated at room temperature (about 25° C.) and under atmospheric pressure.

Example 3

Using a procedure analogous to the above mentioned general method, fluorescent blue emitting organic EL device having the following device structure was produced (See FIG. 1). Device: ITO/HAT-CN (20 nm)/hole transport material (HTM)(110 nm)/electron blocking material (EBM)(5 nm)/H3 doped 5% emitting dopant (30 nm)/HB3 (10 nm)/ET2 doped 50% LiQ (35 nm)/LiQ (1 nm)/Al (160 nm). The I-V-B (at 1000 nits) and half-life time of fluorescent blue emitting organic EL device testing report as Table 1. The half-life time is defined that the initial luminance of 1000 $cd/m^2$ has dropped to half.

TABLE 1

| HTM | EBM | emitting dopant | Voltage (V) | Efficiency (cd/A) | CIE(y) | Half-life time (hour) |
|---|---|---|---|---|---|---|
| EX9 | — | D1 | 3.0 | 5.8 | 0.20 | 280 |
| EX26 | — | D1 | 3.2 | 5.3 | 0.21 | 250 |
| NPB | — | D1 | 3.5 | 5.5 | 0.19 | 180 |
| NPB | EX9 | D1 | 3.8 | 6.0 | 0.21 | 160 |
| NPB | EX26 | D1 | 4.0 | 5.8 | 0.20 | 120 |
| NPB | — | EX3 | 3.5 | 4.2 | 0.16 | 105 |

In the above preferred embodiments for organic EL device test report (see Table 1), we show that the indenotriphenylene-based diamine derivative with a general formula (1) used as hole transport material (HTM), electron blocking material (ETM) for organic EL in the present invention display good performance than the prior art of organic EL materials. More specifically, the organic EL device in the present invention use the indenotriphenylene-based diamine derivative with a general formula (1) as emitting dopant material to collocate with emitting host material H3 shown lower power consumption, and higher efficiency To sum up, the present invention discloses an indenotriphenylene-based diamine derivative with a general formula (1) and their use for hole transport layer, electron blocking layer and fluorescent emitting dopant of emitting layer for organic EL device. The mentioned indenotriphenylene-based diamine derivative are represented by the following formula (1)

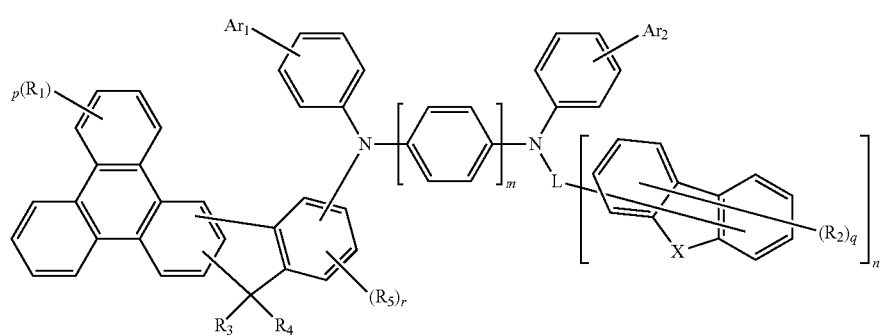

formula (1)

wherein $Ar^1$ and $Ar_2$ represent a hydrogen atom and a substituted or unsubstituted non-fused aryl group having 6~20 carbon atoms, m represent an integer of 0 to 4, r represent an integer of 0 to 3, p and q represent an integer of 0 to 8, n represents an integer of 0 or 1; when n represents an integer of 0, L represents a substituted or unsubstituted divalent arylene group having 6 to 30 carbon atoms, when n represents an integer of 1, L represents a single bond and a substituted or unsubstituted divalent arylene group having 6 to 30 carbon atoms, X represents a divalent bridge selected from the atom or group consisting from O, S, $C(R_6)(R_7)$ and $N(R_8)$, $R_1$ to $R_8$ are independently selected from the group consisting of a hydrogen atom, a substituted or unsubstituted alkyl group having 1 to 20 carbon atoms, a substituted or unsubstituted aryl group having 6 to 30 carbon atoms and a substituted or unsubstituted heteroaryl group having 3 to 30 carbon atoms.

Obvious many modifications and variations are possible in light of the above teachings. It is therefore to be understood that within the scope of the appended claims the present invention can be practiced otherwise than as specifically described herein. Although specific embodiments have been illustrated and described herein, it is obvious to those skilled in the art that many modifications of the present invention may be made without departing from what is intended to be limited solely by the appended claims.

The invention claimed is:

1. An indenotriphenylene-based diamine derivative represented by the following formula (1):

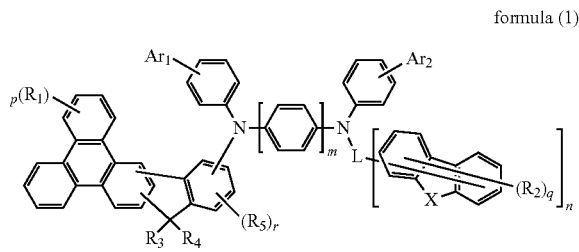

formula (1)

wherein $Ar_1$ and $Ar_2$ independently represent a hydrogen atom, a substituted or unsubstituted alkyl group having 1~20 carbon atoms, or a substituted or unsubstituted non-fused aryl group having 6~20 carbon atoms, m represents an integer of 0 to 4, r represents an integer of 0 to 3, p and q represent an integer of 0 to 8, n represents an integer of 0 or 1; when n represents an integer of 0, L represents a substituted or unsubstituted aryl group having 6 to 30 carbon atoms, when n represents an integer of 1, L represents a single bond or a substituted or unsubstituted divalent arylene group having 6 to 30 carbon atoms, X represents a divalent bridge selected from the atom or group consisting from O, S, $C(R_6)(R_7)$ and $N(R_8)$, $R_1$ to $R_8$ are independently selected from the group consisting of a hydrogen atom, a substituted or unsubstituted alkyl group having 1 to 20 carbon atoms, a substituted or unsubstituted aryl group having 6 to 30 carbon atoms and a substituted or unsubstituted heteroaryl group having 3 to 30 carbon atoms.

2. The indenotriphenylene-based diamine derivative according to claim 1, wherein the indenotriphenylene-based diamine derivative formula (1) is represented by the following formula (2) to formula (4):

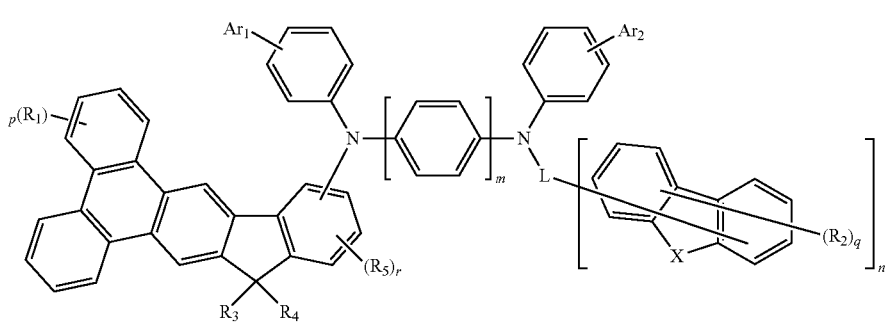

formula (2)

formula (3)

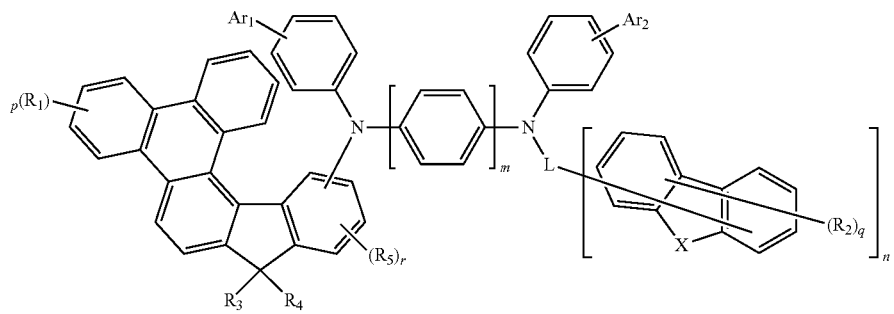

formula (4)

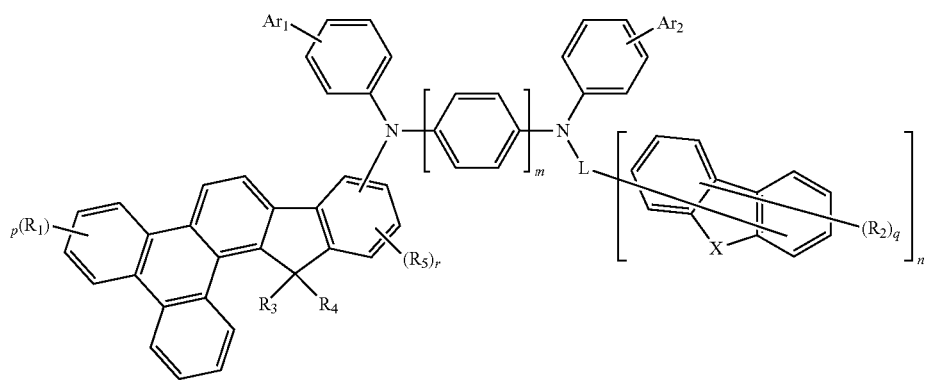

wherein $Ar_1$ and $Ar_2$ independently represent a hydrogen atom, a substituted or unsubstituted alkyl group having 1~20 carbon atoms, or a substituted or unsubstituted non-fused aryl group having 6~20 carbon atoms, m represents an integer of 0 to 4, r represents an integer of 0 to 3, p and q represent an integer of 0 to 8, n represents an integer of 0 or 1; when n represents an integer of 0, L represents a substituted or unsubstituted aryl group having 6 to 30 carbon atoms, when n represents an integer of 1, L represents a single bond or a substituted or unsubstituted divalent arylene group having 6 to 30 carbon atoms, X represents a divalent bridge selected from the atom or group consisting from O, S, $C(R_6)(R_7)$ and $N(R_8)$, $R_1$ to $R_8$ are independently selected from the group consisting of a hydrogen atom, a substituted or unsubstituted alkyl group having 1 to 20 carbon atoms, a substituted or unsubstituted aryl group having 6 to 30 carbon atoms and a substituted or unsubstituted heteroaryl group having 3 to 30 carbon atoms.

3. The indenotriphenylene-based diamine derivative according to claim 2, wherein when m represents an integer of 2, n represents an integer of 1, and L represents a single bond or a substituted or unsubstituted phenylene group, the indenotriphenylene-based diamine derivative formula (2) to formula (4) are represented by the following formula (5) to formula (10):

formula (5)

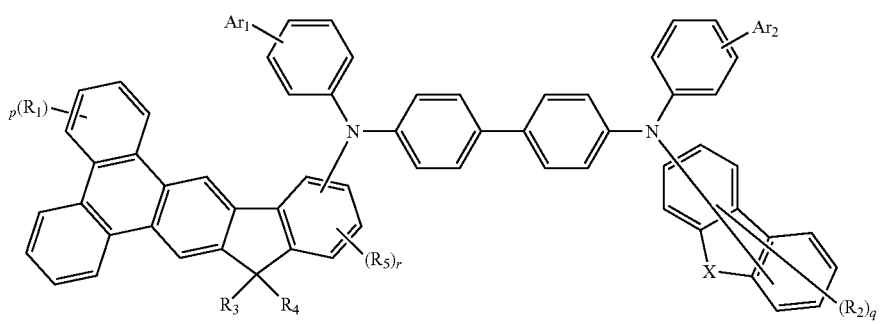

formula (6)
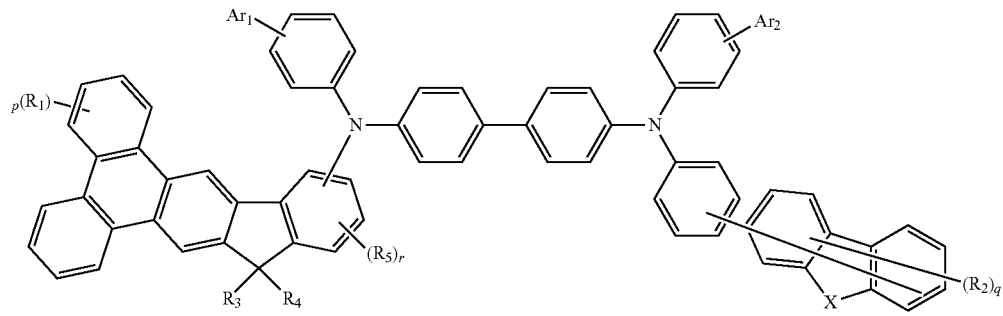
formula (7)
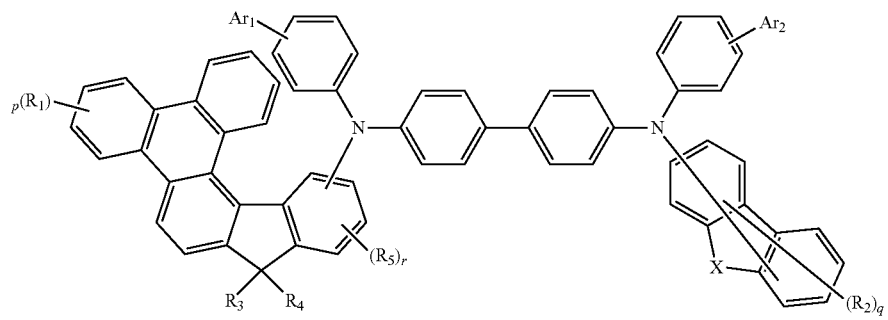
formula (8)
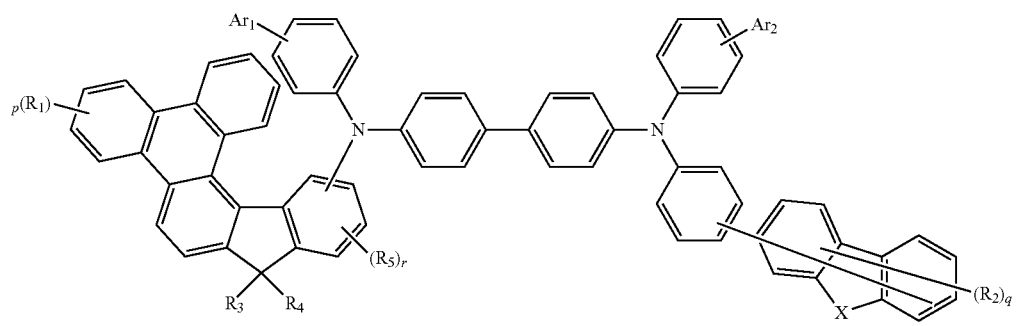
formula (9)
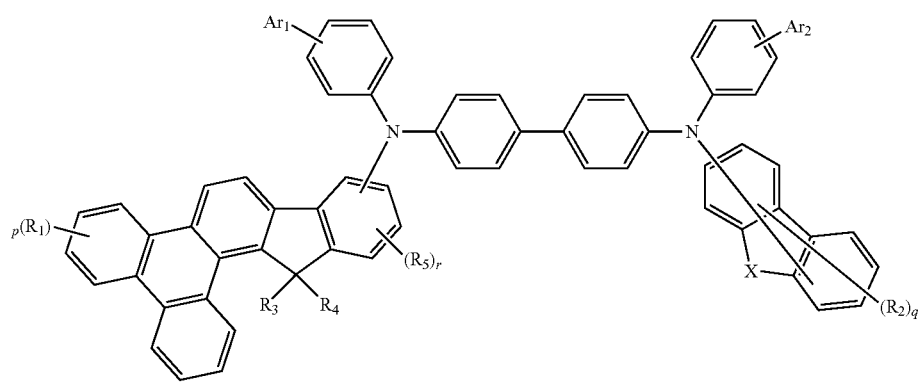

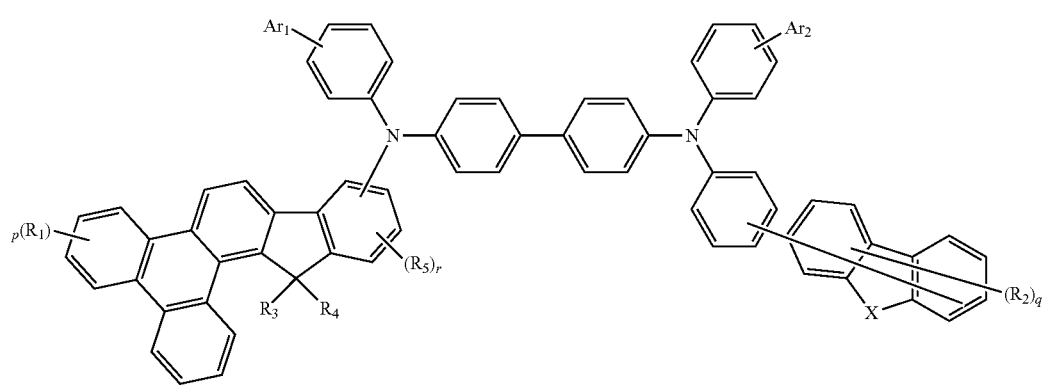

formula (10)

wherein Ar₁ and Ar₂ independently represent a hydrogen atom, a substituted or unsubstituted alkyl group having 1~20 carbon atoms, or a substituted or unsubstituted non-fused aryl group having 6~20 carbon atoms, r represents an integer of 0 to 3, p and q represent an integer of 0 to 8, X represents a divalent bridge selected from the atom or group consisting from O, S, C(R₆)(R₇) and N(R₈), R₁ to R₈ are independently selected from the group consisting of a hydrogen atom, a substituted or unsubstituted alkyl group having 1 to 20 carbon atoms, a substituted or unsubstituted aryl group having 6 to 30 carbon atoms and a substituted or unsubstituted heteroaryl group having 3 to 30 carbon atoms.

4. The indenotriphenylene-based diamine derivative according to claim 3, wherein Ar₁ and Ar₂ are independently represented by one of the following formulas:

5. The indenotriphenylene-based diamine derivative according to claim 1, wherein the indenotriphenylene-based diamine derivative is selected from the following formulas:

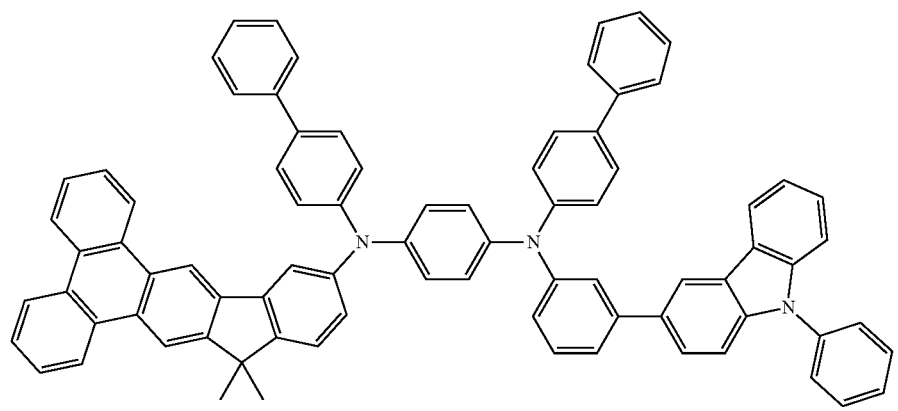

EX1

-continued
EX2
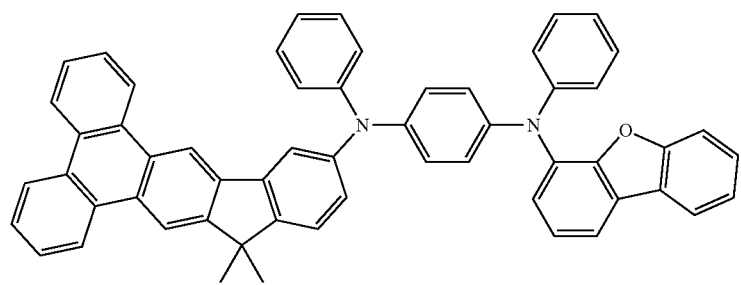
EX3
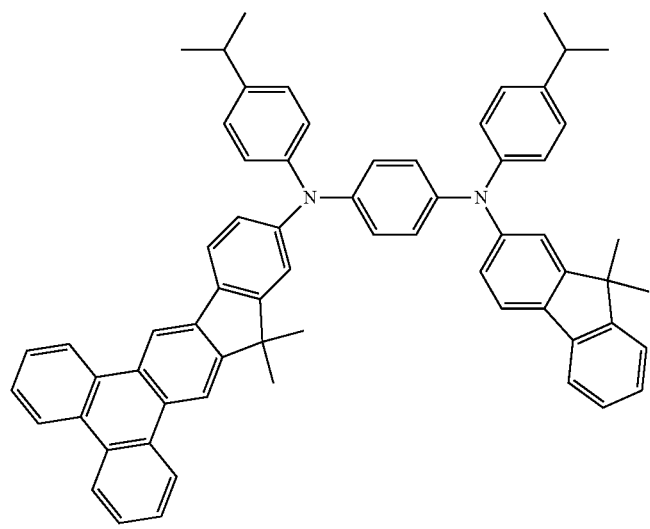
EX4
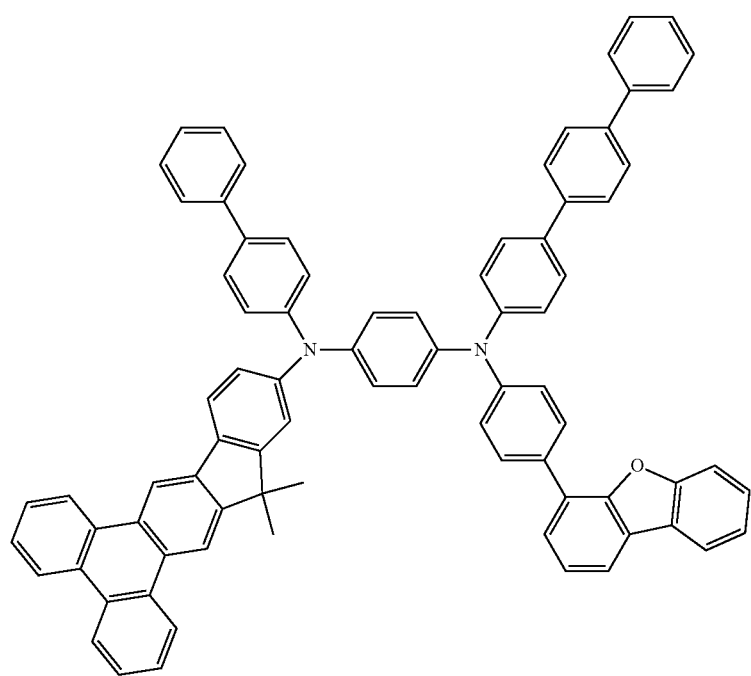

EX5
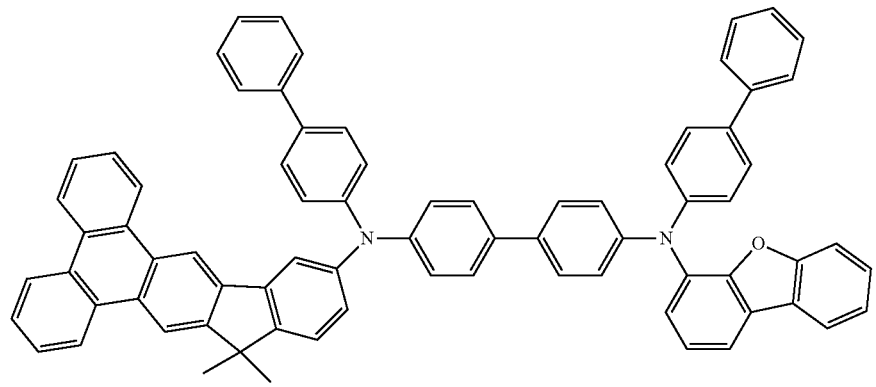
EX6
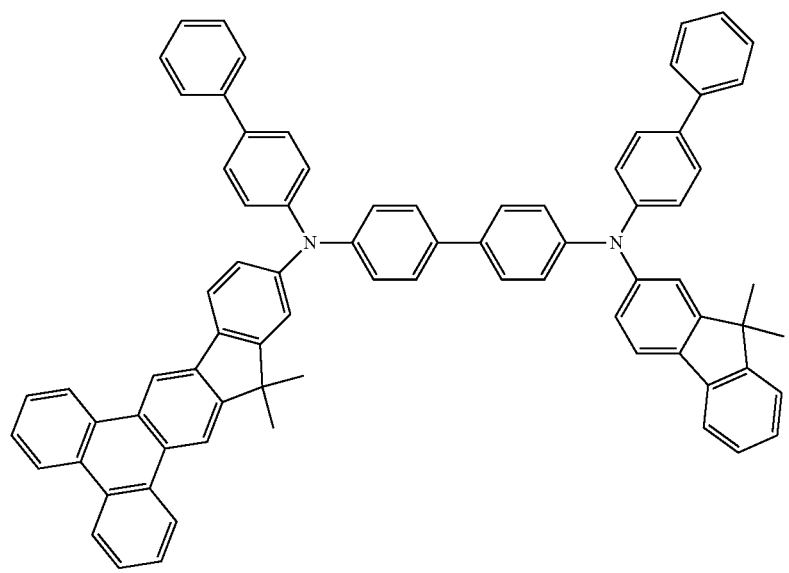
EX7
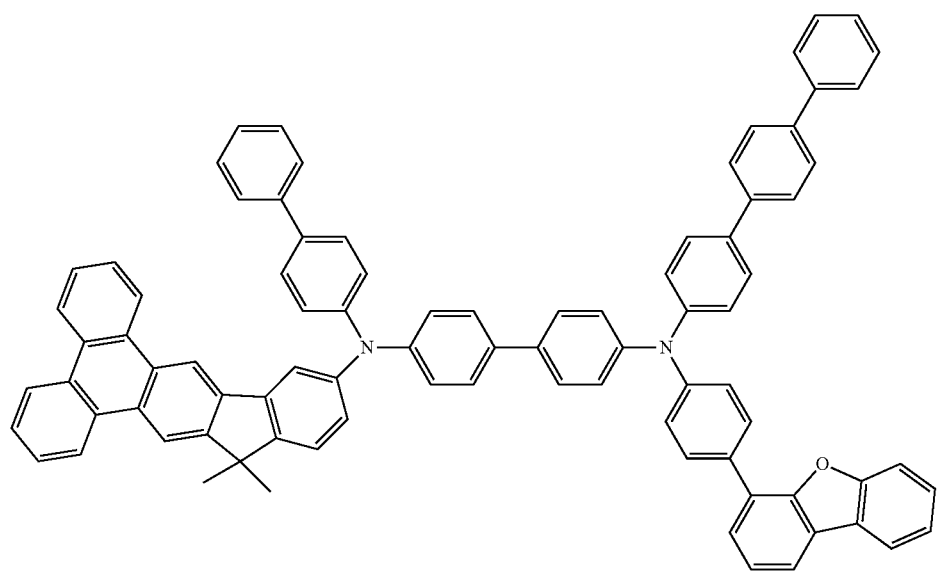

-continued
EX8
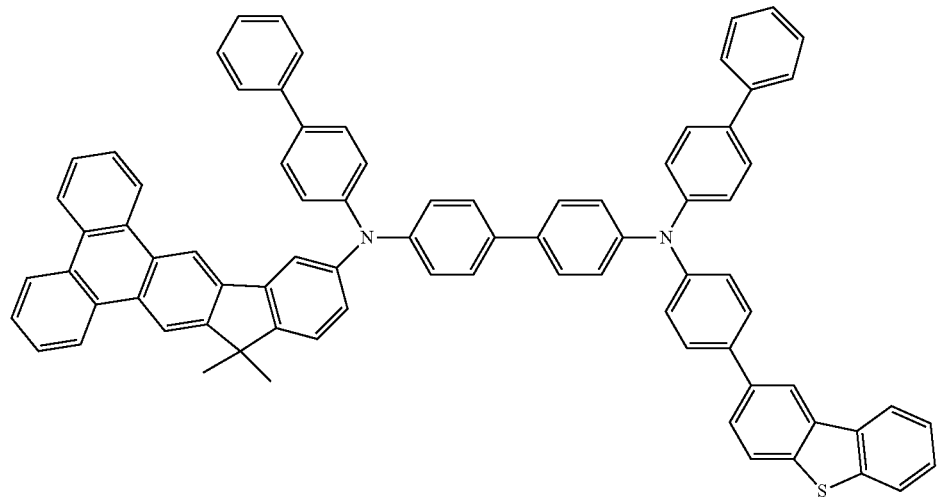
EX9
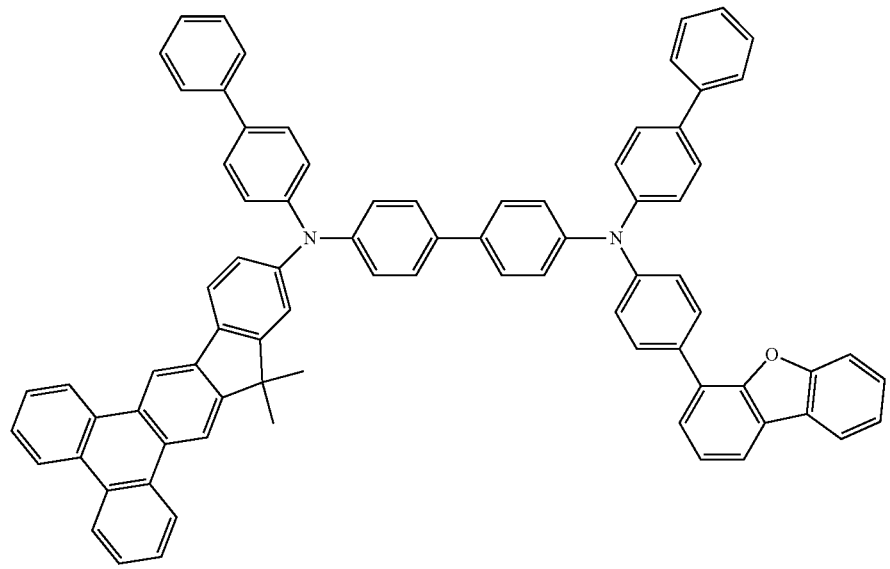
EX10
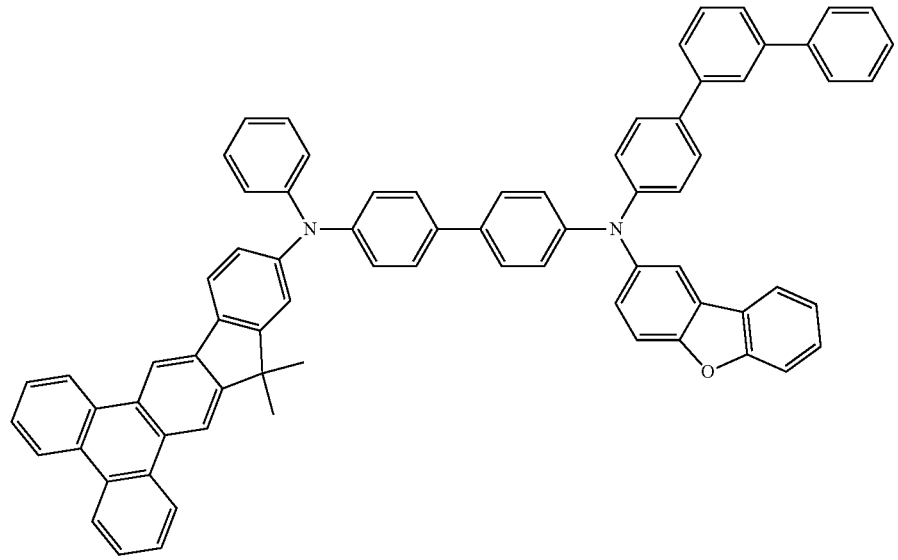

-continued
EX11
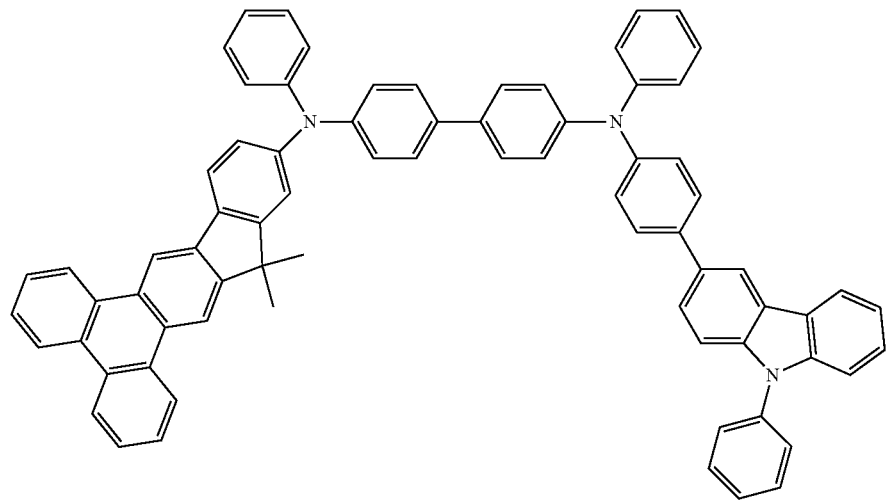
EX12
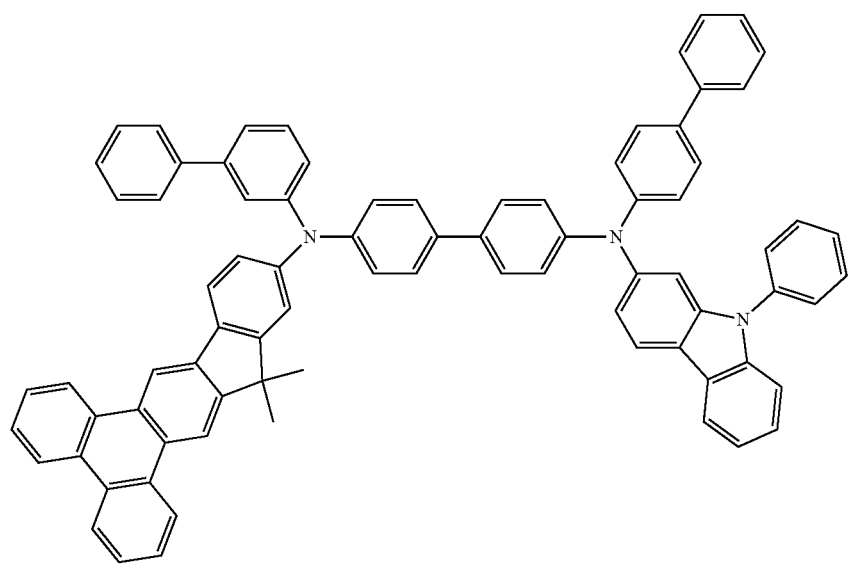
EX13
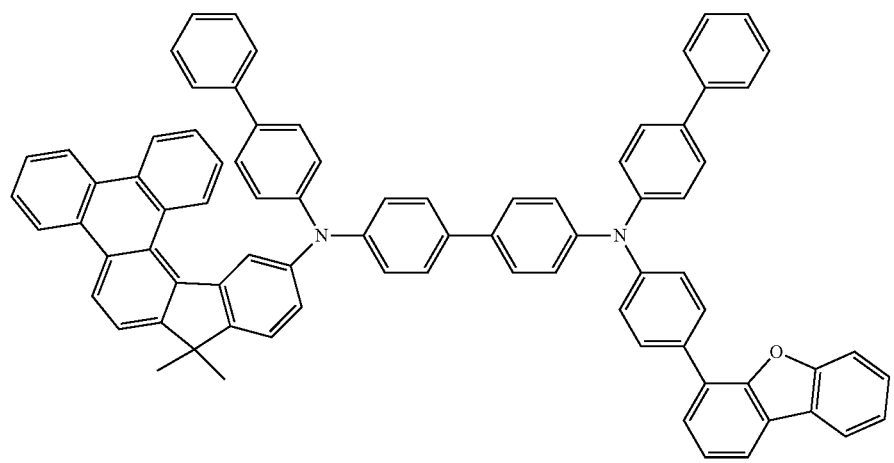

-continued
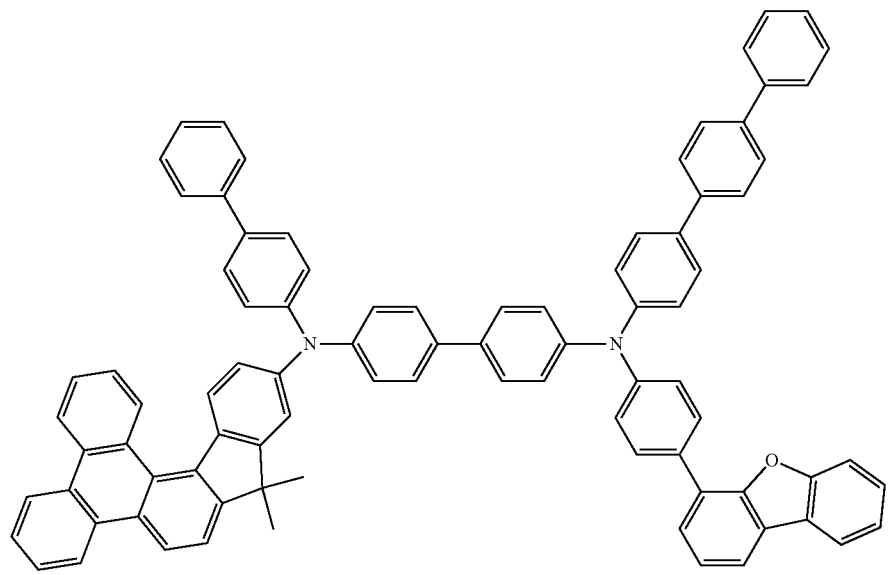
EX14
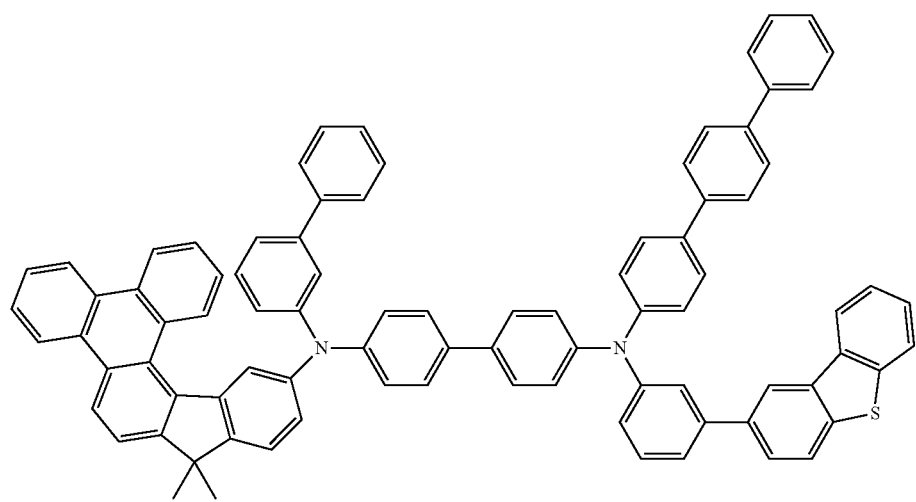
EX15
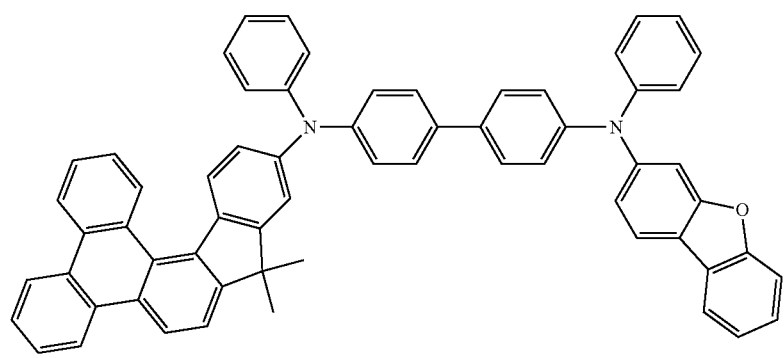
EX16

-continued
EX17
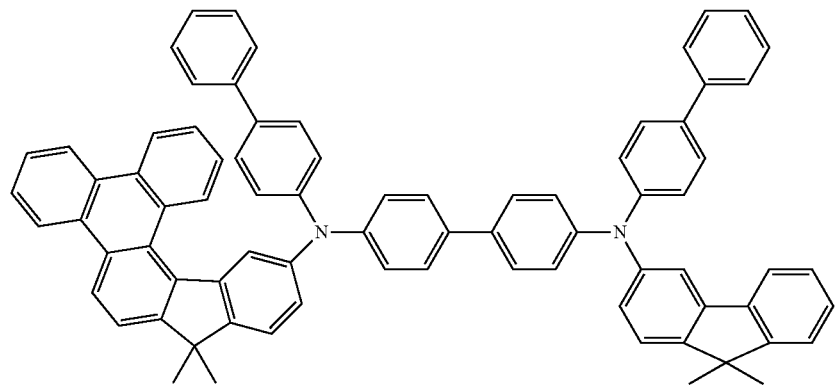
EX18
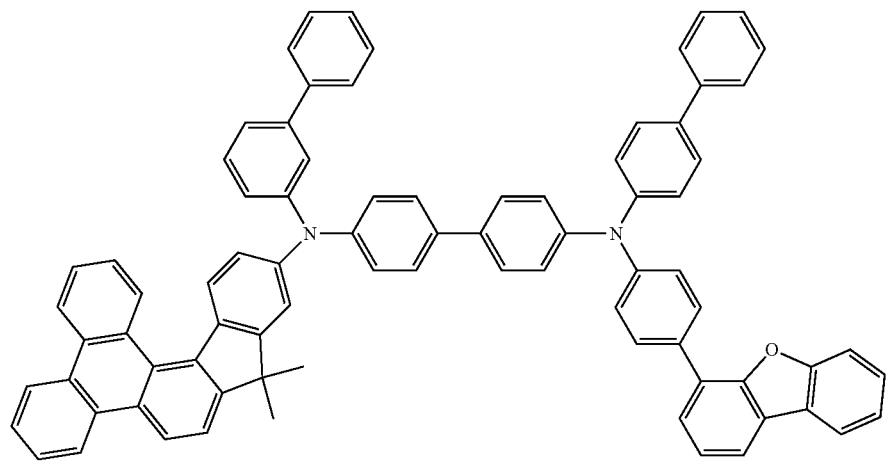
EX19
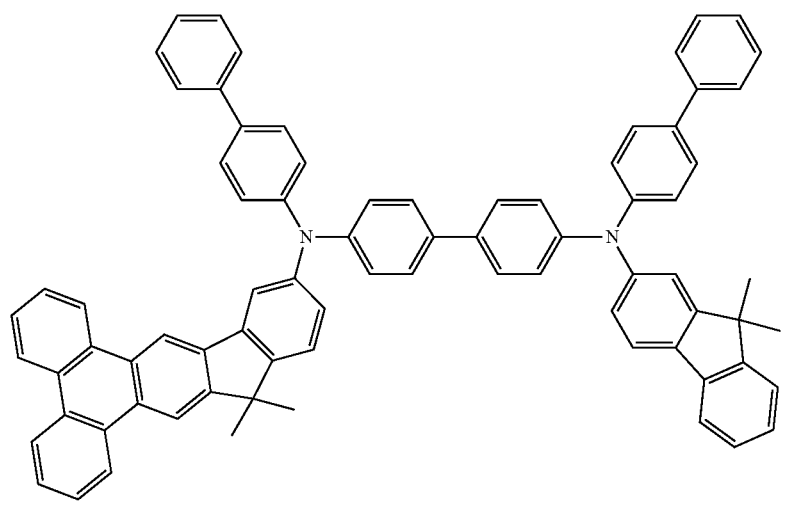

-continued
EX20
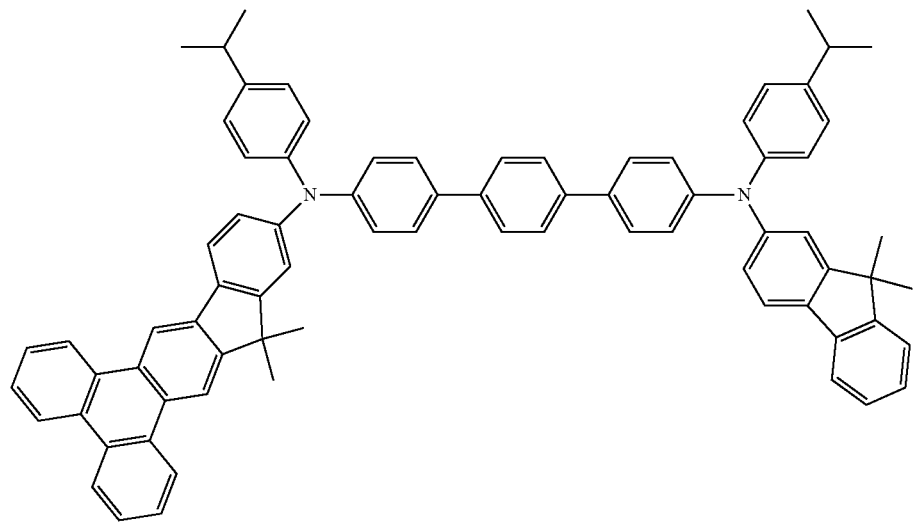
EX21
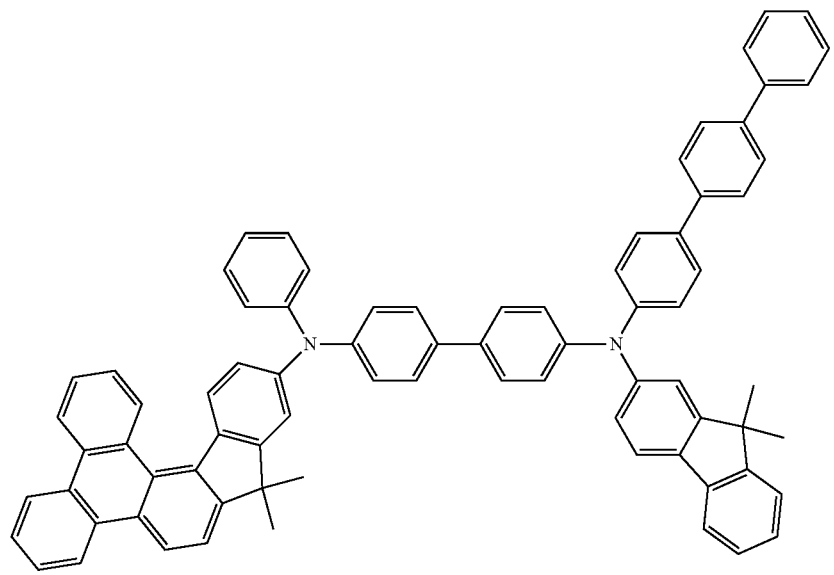
EX22
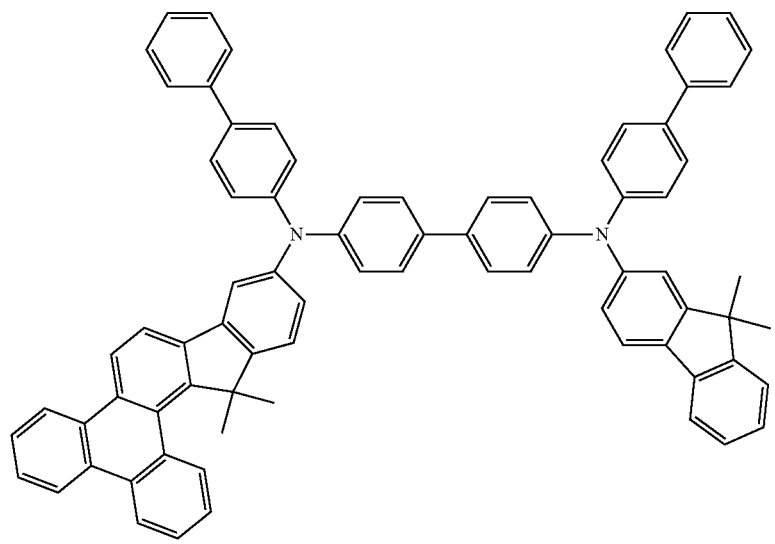

-continued
EX23
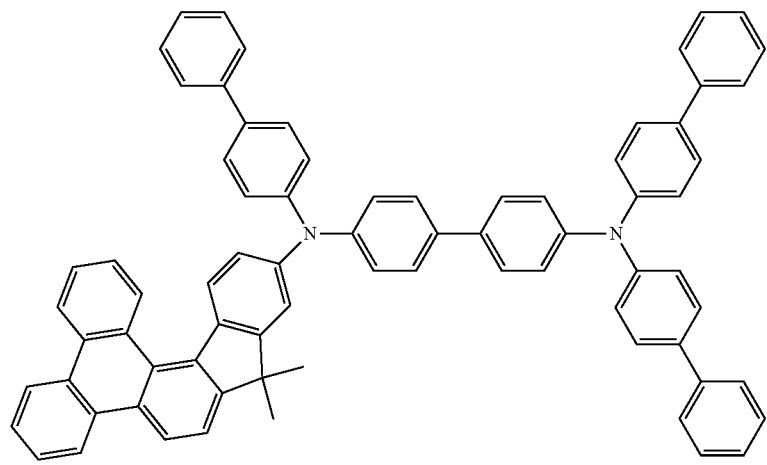
EX24
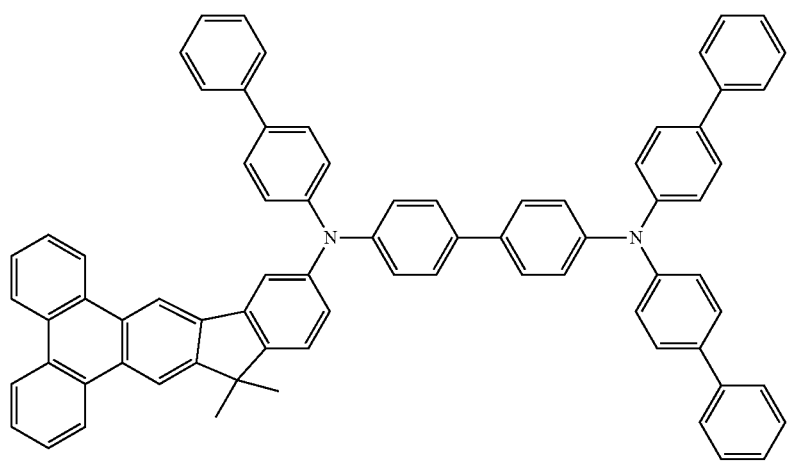
EX25
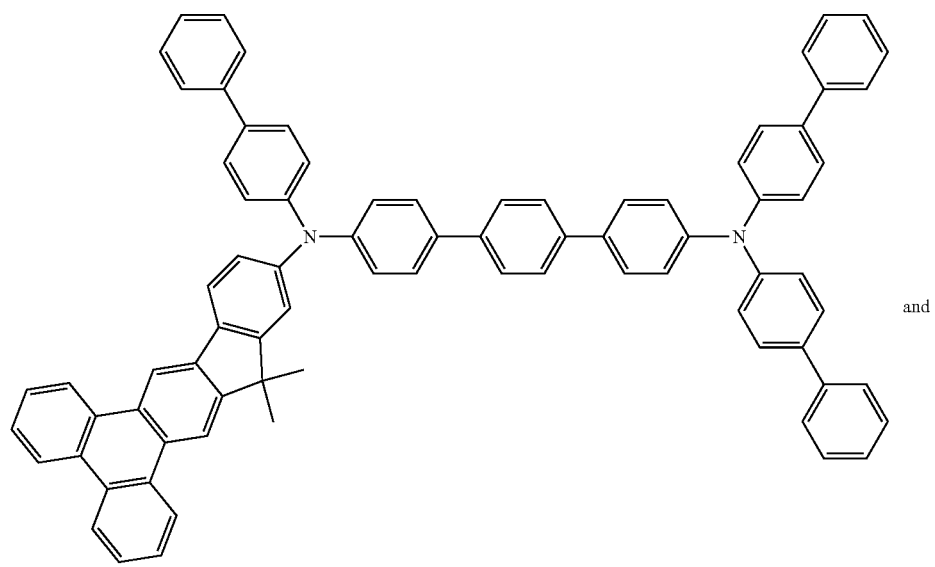
and

-continued

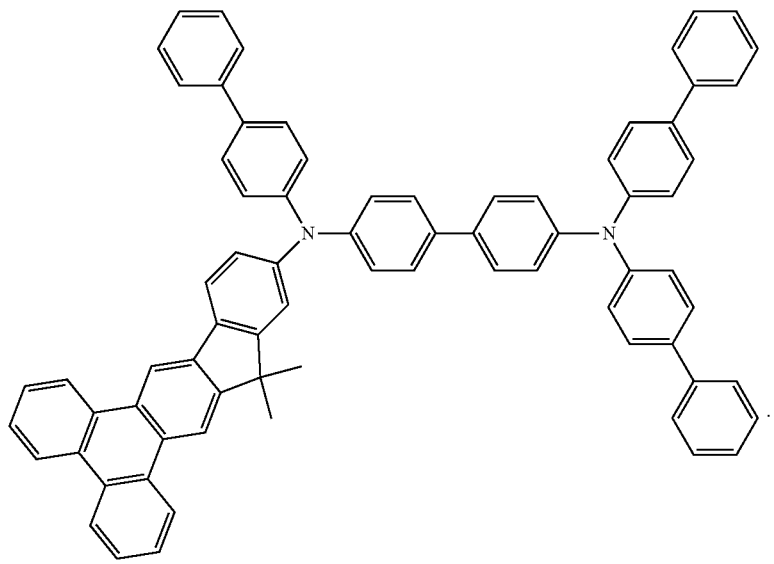

EX26

6. A organic electroluminescent device comprising a pair of electrodes consisting of a cathode and an anode, and between the pairs of electrodes comprising at least a layer of the indenotriphenylene-based diamine derivative with a general formula (1) according to claim 1.

7. The organic electroluminescent device according to claim 6, wherein the hole transport material comprising the indenotriphenylene-based diamine derivative with a general formula (1).

8. The organic electroluminescent device according to claim 6, wherein the hole transport material comprising the indenotriphenylene-based diamine derivative with a general formula (2) to formula (4).

9. The organic electroluminescent device according to claim 6, wherein the hole transport material comprising the indenotriphenylene-based diamine derivative with a general formula (5) to formula (10).

10. The organic electroluminescent device according to claim 6, wherein the electron blocking material comprising the indenotriphenylene-based diamine derivative with a general formula (1).

11. The organic electroluminescent device according to claim 6, wherein the electron blocking material comprising the indenotriphenylene-based diamine derivative with a general formula (2) to formula (4).

12. The organic electroluminescent device according to claim 6, wherein the electron blocking material comprising the indenotriphenylene-based diamine derivative with a general formula (5) to formula (10).

13. The organic electroluminescent device according to claim 6, wherein the fluorescent emitting dopant comprising the indenotriphenylene-based diamine derivative with a general formula (1).

14. The organic electroluminescent device according to claim 13, wherein the fluorescent emitting host comprising the following formulas:

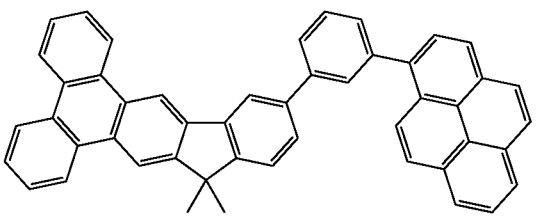

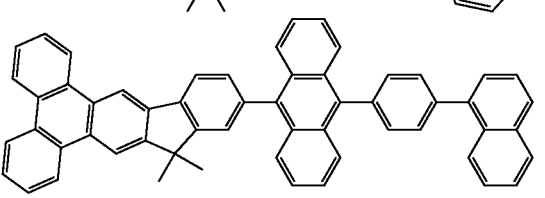

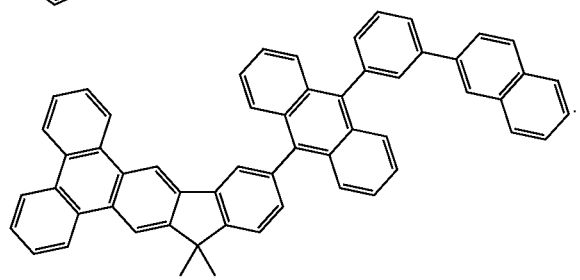

* * * * *